US008741633B2

(12) United States Patent
Nett et al.

(10) Patent No.: US 8,741,633 B2
(45) Date of Patent: Jun. 3, 2014

(54) RECOMBINANT VECTORS

(75) Inventors: Juergen Nett, Grantham, NH (US); Robert Davidson, Enfield, NH (US)

(73) Assignee: Glycofi, Inc., Lebanon, NH (US)

( * ) Notice: Subject to any disclaimer, the term of this patent is extended or adjusted under 35 U.S.C. 154(b) by 508 days.

(21) Appl. No.: 12/227,203

(22) PCT Filed: May 18, 2007

(86) PCT No.: PCT/US2007/012198
§ 371 (c)(1),
(2), (4) Date: Nov. 10, 2008

(87) PCT Pub. No.: WO2007/136865
PCT Pub. Date: Nov. 29, 2007

(65) Prior Publication Data
US 2009/0124000 A1 May 14, 2009

Related U.S. Application Data

(60) Provisional application No. 60/801,688, filed on May 19, 2006.

(51) Int. Cl.
*C12N 15/00* (2006.01)
(52) U.S. Cl.
USPC .................................................. 435/320.1
(58) Field of Classification Search
None
See application file for complete search history.

(56) References Cited

U.S. PATENT DOCUMENTS

| | | | |
|---|---|---|---|
| 4,818,700 A | 4/1989 | Cregg et al. | |
| 7,029,872 B2 | 4/2006 | Gerngross | |
| 7,259,007 B2 | 8/2007 | Bobrowicz et al. | |
| 7,332,299 B2 | 2/2008 | Hamilton | |
| 7,449,308 B2 | 11/2008 | Gerngross et al. | |
| 7,465,577 B2 | 12/2008 | Bobrowicz | |
| 7,479,389 B2 | 1/2009 | Nett et al. | |
| 7,514,253 B2 | 4/2009 | Nett | |
| 2003/0152940 A1 | 8/2003 | Sablon et al. | |
| 2004/0229306 A1 | 11/2004 | Nett | |
| 2005/0089047 A1 | 4/2005 | Ould-Brahim et al. | |
| 2005/0170452 A1 | 8/2005 | Wildt et al. | |
| 2005/0208617 A1 | 9/2005 | Bobrowicz et al. | |
| 2005/0244428 A1* | 11/2005 | Howley et al. | 424/199.1 |
| 2005/0260729 A1 | 11/2005 | Hamilton | |
| 2006/0040353 A1 | 2/2006 | Davidson et al. | |
| 2006/0252096 A1 | 11/2006 | Zha et al. | |
| 2006/0286637 A1 | 12/2006 | Hamilton | |
| 2007/0037248 A1 | 2/2007 | Bobrowicz et al. | |
| 2007/0077642 A1 | 4/2007 | Strauss et al. | |
| 2008/0299616 A1 | 12/2008 | Choi | |
| 2009/0170159 A1 | 7/2009 | Bobrowicz et al. | |
| 2009/0203105 A1* | 8/2009 | Nett | 435/194 |

FOREIGN PATENT DOCUMENTS

| | | | | |
|---|---|---|---|---|
| EP | 695361 | * | 8/2003 | ............ C12N 15/90 |
| WO | 03/027261 | | 4/2003 | |

OTHER PUBLICATIONS

Weyden, "Tools for targeted manipulation of the mouse genome", Physiol. Genomics (2002), vol. 11, pp. 133-164.
Lin Cereghino, "New selectable marker/auxotrophic host strain combinations . . . ", Gene (2001), 159-169, vol. 263.
Cosano, "Yeast sequencing reports", Yeast (1998), 861-867, vol. 14.
Li, "Optimization of humanized IgGs in glycoengineered . . . ", Nature Biotechnol. (2006), 210-215, vol. 24.
Lai, "Structural characterization of human erythropoietin", J. Biol. Chem. (1986), 3116-3121, vol. 261.
Laemmli, "Cleavage of structural proteins during the assembly . . . ", Nature (1970), 680-685, vol. 227.
Hamilton, "Humanization of yeast to produce complex . . . ", Science (2006), 1441-1443, vol. 313.
Hamilton, "Production of complex human glycoproteins in yeast", Science (2003), 1244-1246, vol. 301.
Fukuda, "Survival of recombinant erythropoietin . . . ", Blood (1989), 84-89, vol. 73.
Davis, "Characterization of recombinant human erythropoietin . . . ", Biochemistry (1987), 2633-2638, vol. 26.
Davidson, "Functional analysis of the ALG3 gene encoding . . . ", Glycobiology (2004), 399-407, vol. 14.
Bobrowicz, "Engineering of an artificial glycosylation pathway . . . ", Glycobiology (2004), 757-766, vol. 14.
Ashwell, "Carbohydrate-specific receptors . . . ", Ann. Rev. Biochem. (1982), 531-554, vol. 51.
Stockert, "The asialoglycoprotein receptor: . . . ", Physiol. Reviews (1995), 591-609, vol. 75.
Werten, "High-yield secretion of recombinant gelatins . . . ", Yeast (1999), 1087-1096, vol. 15.
Nett, "Cloning and disruption of the Pichia pastoris ARG1 . . . ", Yeast (2005), 295-304, vol. 22.
Nett, "Cloning and disruption of the PpURA5 gene . . . ", Yeast (2003), 1279-1290, vol. 20.
Gemmill, "Overview of N- and O-linked oligosaccharide structures . . . ", Biochim. et Biophysica. Acta, 227-237, vol. 1426, 1999.
Durand, "Genetic improvement of Trichoderma reesei . . . ", Enzyme Microb. Technol. (1988), 341-346, vol. 10.
Choi, "Use of combinatorial genetic libraries . . . ", PNAS (2003), 5022-5027, vol. 100.
Spivak, "Erythropoietin", Blood Rev. (1989), 130-135, vol. 3.
Accession No. X56180, *P. pastoris* HIS4 gene for trifunctional enzyme (phosphoribosyl-AMP cyclohydroase . . . ; (*Pichia pastoris*), Apr. 18, 2005.
Accession No. AY653304, *Pichia pastoris* Dol-P-Man:Man5GlcNAc2-PP-Dol mannosyltransferase, Aug. 10, 2004.

* cited by examiner

*Primary Examiner* — Anne Gussow
*Assistant Examiner* — Channing S Mahatan

(57) ABSTRACT

Methods and materials are provided for integrating heterologous nucleic acids into the genome of a cell or virus without disrupting expression of genes adjacent to the insertion site.

12 Claims, 10 Drawing Sheets

Transcriptional Terminator, Expression Cassette and Marker are integrated at the stop codon of the knock-in ORF Promoter, Expression Cassette and Marker
are integrated at the start codon of the knock-in ORF

SEQUENCE LISTING

<160> NUMBER OF SEQ ID NOS: 11

<210> SEQ ID NO 1
<211> LENGTH: 32
<212> TYPE: DNA
<213> ORGANISM: Artificial Sequence
<220> FEATURE:
<223> OTHER INFORMATION: rEPO-forward PCR Primer

<400> SEQUENCE: 1
gggaattcgc tcccccacgc ctcatttgcg ac          32

<210> SEQ ID NO 2
<211> LENGTH: 32
<212> TYPE: DNA
<213> ORGANISM: Artificial Sequence
<220> FEATURE:
<223> OTHER INFORMATION: rEPO-reverse PCR Primer

<400> SEQUENCE: 2
cctctagatc acctgtcccc tctcctgcag gc          32

<210> SEQ ID NO 3
<211> LENGTH: 46
<212> TYPE: DNA
<213> ORGANISM: Artificial Sequence
<220> FEATURE:
<223> OTHER INFORMATION: ScMnt1-forward PCR primer

<400> SEQUENCE: 3
gggcggccgc caccatggcc ctctttctca gtaagagact gttgag          46

<210> SEQ ID NO 4
<211> LENGTH: 43
<212> TYPE: DNA
<213> ORGANISM: Artificial Sequence
<220> FEATURE:
<223> OTHER INFORMATION: ScMnt1-reverse PCR primer

<400> SEQUENCE: 4
ccggcgcgcc cgatgacttg ttgttcaggg gatatagatc ctg          43

<210> SEQ ID NO 5
<211> LENGTH: 2652
<212> TYPE: DNA
<213> ORGANISM: Artificial Sequence
<220> FEATURE:
<223> OTHER INFORMATION: Pichia pastoris PRO1 gene (incomplete)
<220> FEATURE:
<221> NAME/KEY: misc_feature
<222> LOCATION: (1225)...(1227)
<223> OTHER INFORMATION: Stop codon

<400> SEQUENCE: 5
ggccatcgaa ttgtcatcgt ctcctcaggt gccatcgctg tgggcatgaa gagagtcaac          60
atgaagcgga aaccaaaaaa gttacagcaa gtgcaggcat tggctgctat aggacaaggc          120

```
cgtttgatag actttggga cgacctttc cgtcagttga atcagcctat tgcgcagatt        180
ttactgacta gaacggattt ggtcgattac acccagttta agaacgctga aaatacattg        240
gaacagctta ttaaaatggg tattattcct attgtcaatg agaatgacac cctatccatt        300
caagaaatca aatttggtga caatgacacc ttatccgcca taacagctgg tatgtgtcat        360
gcagactacc tgttttggt gactgatgtg gactgtcttt acacggataa ccctcgtacg        420
aatccggacg ctgagccaat cgtgttagtt agaaatatga ggaatctaaa cgtcaatacc        480
gaaagtggag gttccgccgt aggaacagga ggaatgacaa ctaaattgat cgcagctgat        540
ttgggtgtat ctgcaggtgt tacaacgatt atttgcaaaa gtgaacatcc cgagcagatt        600
ttggacattg tagagtacag tatccgtgct gatagagtcg aaaatgaggc taaatatctg        660
gtcatcaacg aagaggaaac tgtggaacaa tttcaagaga tcaatcggtc agaactgagg        720
gagttgaaca agctggacat tcctttgcat acacgtttcg ttggccacag ttttaatgct        780
gttaataaca aagagttttg gttactccat ggactaaagg ccaacggagc cattatcatt        840
gatccaggtt gttataaggc tatcactaga aaaacaaag ctggtattct tccagctgga        900 attattccg tagagggtaa tttccatgaa tacgagtgtg ttgatgttaa ggtaggacta        960
agagatccag atgacccaca ttcactagac cccaatgaag aactttacgt cgttggccgt       1020
gcccgttgta attccccag caatcaaatc aacaaaatta agggtctaca agctcgcag       1080 atcgagcagg ttctaggtta cgctgacggt gagtatgttg ttcacaggga caacttggct       1140
ttcccagtat ttgccgatcc agaactgttg gatgttgttg agagtaccct gtctgaacag       1200
gagagagaat ccaaaccaaa taatagaat ttcacatatg ctgcttgatt atgtaattat       1260
accttgcgtt cgatggcatc gattccctct tctgtcaatc gcgcatcgca ttaaaagtat       1320
actttttttt ttttcctata gtactattcg ccttattata aactttgcta gtatgagttc       1380
tacccccaag aaagagcctg atttgactcc taagaagagt cagcctccaa agaatagtct       1440
cggtgggggt aaaggcttta gtgaggaggg tttctcccaa ggggacttca gcgctaagca       1500
tatactaaat cgtcgcccta acaccgaagg ctcttctgtg gcttcgaacg tcatcagttc       1560
gtcatcattg caaaggttac catcctctgg atctggaagc gttgctgtgg aagtgtgtt       1620 gggatcttcg ccattaactc tttctggagg gttccacggg cttgatccaa ccaagaataa       1680
aatagacgtt ccaaagtcga aacagtcaag gagacaaagt gttctttctg acatgatttc       1740
cacttctcat gcagctagaa atgatcactc agagcagcag ttacaaactg acaacaatc       1800 agaacaaaaa gaagaagatg gtagtcgatc ttctttttct gtttcttccc ccgcaagaga       1860
tatccggcac ccagatgtac tgaaaactgt cgagaaacat cttgccaatg acagcgagat       1920
cgactcatct ttcaacttc aaggtggaga tgtcactaga ggcatttatc aatgggtaac       1980
tggagaaagt agtcaaaaag ataacccgcc tttgaaacga gcaaatagtt ttaatgattt       2040
ttcttctgtg catggtgacg aggtaggcaa ggcagatgct gaccacgatc gtgaaagcgt       2100
attcgacgag gatgatatct ccattgatga tatcaaagtt ccgggaggga tgcgtcgaag       2160 tttttttatta caaaagcata gagaccaaca actttctgga ctgaataaaa cggctcacca       2220
accaaaacaa cttactaaac ctaatttctt cacgaacaac tttatagagt ttttggcatt       2280
gtatgggcat tttgcaggtg aagatttgga ggaagacgaa gatgaagatt tagacagtgg       2340
ttccgaatca gtcgcagtca gtgatagtga gggagaattc agtgaggctg acaacaattt       2400
gttgtatgat gaagagtctc tcctattagc acctagtacc tccaactatg cgagatcaag       2460
aataggaagt attcgtactc ctacttatgg atctttcagt tcaaatgttg gttcttcgtc       2520
```

```
tattcatcag cagttaatga aaagtcaaat cccgaagctg aagaaacgtg acagcacaa    2580 gcataaaaca caatcaaaaa tacgctcgaa gaagcaaact accaccgtaa aagcagtgtt   2640
gctgctatta aa                                                      2652
```

<210> SEQ ID NO 6
<211> LENGTH: 2387
<212> TYPE: DNA
<213> ORGANISM: Artificial Sequence
<220> FEATURE:
<223> OTHER INFORMATION: Pichia pastoris TRP2 gene (incomplete)
<220> FEATURE:
<221> NAME/KEY: misc_feature
<222> LOCATION: (1300)...(1302)
<223> OTHER INFORMATION: Stop codon

<400> SEQUENCE: 6

```
actgggcctt tagagggtgc tgaagttgac cccttggtgc ttctggaaaa agaactgaag     60
ggcaccagac aagcgcaact tcctggtatt cctcgtctaa gtggtggtgc cataggatac    120
atctcgtacg attgtattaa gtactttgaa ccaaaaactg aaagaaaact gaaagatgtt    180
ttgcaacttc cggaagcagc tttgatgttg ttcgacacga tcgtggcttt tgacaatgtt    240
tatcaaagat tccaggtaat tggaaacgtt tctctatccg ttgatgactc ggacgaagct    300
attcttgaga atattataa acaagagaa gaagtggaaa agatcagtaa agtggtatttt    360 gacaataaaa ctgttcccta ctatgaacag aaagatatta ttcaaggcca aacgttcacc    420
tctaatattg gtcaggaagg gtatgaaaac catgttcgca agctgaaaga acatattctg    480
aaaggagaca tcttccaagc tgttccctct caaagggtag ccaggccgac ctcattgcac    540
cctttcaaca tctatcgtca tttgagaact gtcaatcctt ctccatacat gttctatatt    600
gactatctag acttccaagt tgttggtgct tcacctgaat tactagttaa atccgacaac    660
aacaacaaaa tcatcacaca tcctattgct ggaactcttc ccagaggtaa aactatcgaa    720
gaggacgaca attatgctaa gcaattgaag tcgtcttta aagacagggc cgagcacgtc    780
atgctggtag atttggccag aaatgatatt aaccgtgtgt gtgagcccac cagtaccacg    840
gttgatcgtt tattgactgt ggagagattt tctcatgtga tgcatcttgt gtcagaagtc    900
agtggaacat tgagaccaaa caagactcgc ttcgatgctt tcagatccat tttcccagca    960
ggtaccgtct ccggtgctcc gaaggtaaga gcaatgcaac tcataggaga attggaagga   1020
gaaaagagag gtgtttatgc gggggccgta ggacactggt cgtacgatgg aaaatcgatg   1080
gacacatgta ttgccttaag aacaatggtc gtcaaggacg gtgtcgctta ccttcaagcc   1140
ggaggtggaa ttgtctacga ttctgacccc tatgacgagt acatcgaaac catgaacaaa   1200
atgagatcca acaataacac catcttggag gctgagaaaa tctggaccga taggttggcc   1260
agagacgaga atcaaagtga atccgaagaa acgatcaat gaacggagga cgtaagtagg   1320
aatttatgta atcatgccaa tacatcttta gatttcttcc tcttcttttt aacgaaagac   1380
ctccagtttt gcactctcga ctctctagta tcttcccatt tctgttgctg caacctcttg   1440
ccttctgttt cctcaattg ttcttctttc ttctgttgca cttggccttc ttcctccatc   1500
tttcgttttt tttcaagcct tttcagcagt tcttcttcca agagcagttc tttgattttc   1560
tctctccaat ccaccaaaaa actgatgaa ttcaaccggg catcatcaat gttccacttt   1620 ctttctcttta tcaataatct acgtgcttcg gcatacgagg aatccagttg ctccctaatc   1680
gagtcatcca aaggttagc atgggccttt ttcagggtgt caaaagcatc tggagctcgt   1740
ttattcggag tcttgtctgg atggatcagc aaagactttt tgcggaaagt ctttcttata   1800
```

```
tcttccggag aacaacctgg tttcaaatcc aagatggcat agctgtccaa tttgaaagtg   1860
gaaagaatcc tgccaatttc cttctctcgt gtcagctcgt tctcctcctt ttgcaacagg   1920
tccacttcat ctggcatttt tctttatgtt aactttaatt attattaatt ataaagttga   1980
ttatcgttat caaaataatc atattcgaga ataatccgt ccatgcaata tataaataag    2040
aattcataat aatgtaatga taacagtacc tctgatgacc tttgatgaac cgcaattttc   2100
tttccaatga caagacatcc ctataataca attatacagt ttatatatca caaataatca   2160 ccttttttata agaaaaccgt cctctccgta acagaactta ttatccgcac gttatggtta  2220
acacactact aataccgata tagtgtatga agtcgctacg agatagccat ccaggaaact   2280
taccaattca tcagcacttt catgatccga ttgttggctt tattctttgc gagacagata   2340
cttgccaatg aaataactga tcccacagat gagaatccgg tgctcgt              2387
```

<210> SEQ ID NO 7
<211> LENGTH: 978
<212> TYPE: DNA
<213> ORGANISM: Artificial Sequence
<220> FEATURE:
<223> OTHER INFORMATION: Pichia pastoris TRP5 gene (incomplete)
<220> FEATURE:
<221> NAME/KEY: misc_feature
<222> LOCATION: (363)...(365)
<223> OTHER INFORMATION: Stop codon

<400> SEQUENCE: 7

```
acgacggcca aattcatgat acacactctg tttcagctgg tttggactac cctggagttg    60
gtcctgaatt ggctgcctgg aaagcaaatg gtagagccca attttccgct gtaactgatg   120
cccaagcatt agagggattc aaaatccgt ctcaattgga agggatcatt ccagcactag    180
agtctagtca tgcaatctac ggcgcattgc aaattgcaaa gactatgtct tcggaccagt   240
ccttagttat taatgtatct ggaaggggtg ataaggacgt ccagagtgta gctgagattt   300
tacctaaatt gggacctcaa attggatggg atttgcgttt cagcgaagac attactaaag   360
agtgatcgat agcacaatat tcaacttgac tgggtgttaa gaactaagag ctctgggaaa   420 cttttgtattt attactacca acacagtcaa attattggat gtgttttttt ttccagtaca   480
tttcactgag cagtttgtta tactcggtct ttaatctcca tatacatgca gattgtaata   540
cagatctgaa cagtttgatt ctgattgatc ttgccaccaa tattctattt ttgtatcaag   600
taacagagtc aatgatcatt ggtaacgtaa cggttttcgt gtatagtagt tagagcccat   660
cttgtaacct catttcctcc catattaaag tatcagtgat tcgctggaac gattaactaa   720 gaaaaaaaa atatctgcac atactcatca gtctgtaaat ctaagtcaaa actgctgtat    780
ccaatagaaa tcgggatata cctggatgtt ttttccacat aaacaaacgg gagttcagct   840
tacttatggt gttgatgcaa ttcagtatga tcctaccaat aaaacgaaac tttgggattt   900
tggctgtttg agggatcaaa agctgcacct ttacaagatt gacggatcga ccattagacc   960
aaagcaaatg gccaccaa                                                  978
```

<210> SEQ ID NO 8
<211> LENGTH: 1946
<212> TYPE: DNA
<213> ORGANISM: Artificial Sequence
<220> FEATURE:
<223> OTHER INFORMATION: Pichia pastoris Thr1 gene (incomplete)
<220> FEATURE:
<221> NAME/KEY: misc_feature
<222> LOCATION: (1354)...(1356)
<223> OTHER INFORMATION: Stop codon

```
<400> SEQUENCE: 8
gagtcggcca gcccatcacc atgaatgctt aaaacgccaa ctccttccat ctcatttcg      60
taccagatta tgactcttag gcggggagaa tcccgtccag catagcgaac atttcttttt     120
tttttttttt tcgtttcgca tctctctatc gcattcagaa aaaatacat ataattcttc     180
cagtttccgt cattcattac gtttaaaact acgaaagttt tagctctctt ttgttttttgt    240
ttcctagatt cgaaatattt tctttattga gtttaatttg tgtggcagac aatggttaga    300
tctttcacca tcaaagtgcc tgcttcctca gcaaatatag gaccggggtt tgacgttctg    360
ggaattggtc tcaacctta cttggaacta caagtcacca ttgatcccaa aattgatacc     420
tcaagcgatc cagaaaatgt gttattgtcg tatgaaggtg aggggctga tgaggtgtca     480
ttgaaaagtg acgaaaactt gattacgcgc acagctctct atgttctacg ttgtgacgac    540
gtcaggactt tccctaaggg aaccaagatt cacgtcatta accctatcc tctaggaaga    600
ggcttgggat cttcgggtgc tgcagttgtc gccggtgcat tgctcggaaa ttccatcgga    660
cagcttggat actccaaaca acgtttactg gattactgtt tgatgataga acgtcatcca    720
gataacatca ccgcagctat ggtggtggt ttcgttggat cttatcttag agatctttca     780
ccagaagaca cccagagaaa agagattca ttagcagaag tcctgccaga acctcaaggt    840
ggtattaaca ccggtctcaa cccaccagtg cctccaaaaa acattgggca ccacatcaaa    900
tacggctggg caaaagagat caaatgtatt gccattattc cagactttga agtatcaacc    960
gcttcatcta gaggcgttct tccaaccact tacgagagac atgacattat tttcaacctg   1020
caaaggatag ccgttcttac cactgccctg acacaatctc caccagatcc aagcttgata   1080
tacccagcta tgcaggacag gattcaccaa ccttacagga aactttgat ccacggactg   1140
actgaaatac tgtcttcatt cacccccagaa ttacacaaag gtttgttggg aatctgtctt   1200
tccggtgctg ggcccacaat attagccctc gcaactgaaa acttcgatca gattgctaag   1260
gacatcattg ccagatttgc tgtcgaagac atcacctgta gttggaaact cttgaccca    1320
gctcttgaag gttctgttgt tgaggagctt gcttaataga aattagaaca tcctctttag   1380
attatgataa tacgttttta acttttcccc taactgtagt gatggtatct gaccctctta   1440
gaccttaggt tggaccttct cgaatttcct gcctctatca aaaatccgac cctcgacatc   1500
gtttacgtac tttgcaacca attaactagt accggcagac gttcagtgat catggctctc   1560
tatacaaata ccctgataac gtttgcattc ctgacagtcg gaggatgtac gtgcttattt    1620
tcttgctagt cccaaatgtt ttgagattgc tccaatcgtt ttttcaacaa tactaactgc   1680
caacaaatag atcttttatt caacggaaat ggggaacaat tcaacgtggg tgacttttg    1740
gagactacat ctccctatat gtgggcaaat ctgggtatag caagttgcat tggattctcg   1800
gtcattggtg ctgcatgggg aattttcata acaggttctt cgatcatcgg tgcaggtgtc    1860
aaagctccca gaatcacaac aaaaaattta atctccatca ttttctgtga ggtggtggct   1920
atttatgggc ttattatggc cattgt                                          1946

<210> SEQ ID NO 9
<211> LENGTH: 2581
<212> TYPE: DNA
<213> ORGANISM: Artificial Sequence
<220> FEATURE:
<223> OTHER INFORMATION: Pichia pastoris Lys1 gene (incomplete)
<220> FEATURE:
<221> NAME/KEY: misc_feature
<222> LOCATION: (1051)...(1053)
<223> OTHER INFORMATION: Stop codon
```

-continued

```
<400> SEQUENCE: 9
agagccgccc ttacaccttc gacagccaag gaattgttag atacaggaag atttgaaatc      60
tttgttgagg aaagtagtca aagcactttt gcaaccgaag agtataaaaa ggcgggcaca     120
aatattgtac cggaaggttc ctgggttgat gccccaaaag agagaataat tctggggctg     180
aaggaactcc cagaggacac ttttccctta gtacacgagc atattcaatt tgcacactgc     240
tacaaagacc agtccggctg gaaagatgtg ttaaaaagat ttcccgaagg aaatggcact     300
ctttatgatc tggagttctt ggaaaatgat aatggaagaa gagtagctgc ttttggcttc     360
tatgcaggat ttgcaggcgc tgctcttggg attcaagact gggcgttcaa acagacccat     420
gcggatcatg agaatttacc cggtgtttcc ccctatggca acgagcaagc cttgatcgcc     480
gacgttaaaa aagatttgga tgttgccgtt tccaaaactg gaagaaaacc aaagatcttg     540
gttattggtg cccttggtcg ttgtggatct ggtgctattg acttacttaa gaaagtgggt     600
attcccgatg agaacatctc taagtgggac gttaacgaaa ccagtatcgg aggccctttc     660
aaacaaattg cagagtccga catattcatt aattgtatat acctctcaca gccaattcct     720 cctttttatcg acttgaatac tctaaacttc gaggacagag ctctaagaac aattgtggat     780
gtttctgcgg acaccaccaa cccacacaat ccaatccctg tttatactgt tgcgacagta     840
ttttcagatc caacggttcc ggtagaaacc tccaaaggac ctaaactttc tgttgtttct     900
atcgaccatc ttccatcctt gttacccagg gaagcatcag agttttttgt cagagactta     960
ttgccttact tgaaacagtt accggaaagg aagactgctc ccgtttggaa aagagctaaa    1020
gatttatttg atcatcatgt cgaaagactt taatgatatt ctggttgttt agctgctttg    1080
aagtgtttca tcttaaaata tatacttatt cgtacacaat gcttaccaaa ctcttattag    1140
tgtccaagtc ttctgtagag gcagttgttc cgttcaatag cacctcagct tcactgtcaa    1200
aatcactgtc ctctgcctca aatttggggg ttgtttttttt tacattcttc aagtcctcta    1260
tgttttcatt cattgtagta actaccgtaa ggcgctcgct agtagcatac actgcaactt    1320
ggtcaaaagt ttttaagctc cagacaacaa tcttaccatc agaggcaact gatactaaaa    1380
atgagtcttt tgagtcatcg tcttgataaa tgcttatgtc ctttacgcga gttgaatgac    1440
ccaagagttt gtaatcaggt tgaagcttct ccacatctcc tagaaagcac tcatatgaat    1500
aaaaacagat ctccccatta ctatgacaag tgattaagta ttctttttct agctgcacaa    1560
cctcaatttt cattattgtg gactgaaagg gaatatttgt gagaagcttt gcggtcctag    1620
tatggtagac aaatattctg ttgaccaagg caacaataaa atgctcccca tcaaaagacc    1680
atttaacaaa gtgaccggat tgtcctaaag tatcctttcc tttcattttt agggttgatg    1740
ccagcttgga actcatgagg ttccacagtc ttattgtttt atcgttactg accgagactg    1800
caacttttcc actagggtga attgccaagt catttaccgc agctttatga cccttcagca    1860
cagctactgg ctcccagtct ttagttctcc aaacgatgat tgacccatct tcacttcctg    1920
aaagtagcca tttaccatcc gcatccctag ctttagaact ctctcggctg aacttcaagc    1980
aagttatcga acctgtatgt tgcagtaagc ttccaatctc ttttcttttt tggagatcat    2040
aaatctttat atgctcgtcg ttagagccgc taaccaaata ccgctttgcc tgatctaacg    2100
ctctgatgct taaagaatga gcttcgaagt gaaaaatagg ctgaaaaata ggtgtcttct    2160
cagaactcgg ttcgcaactg acagtaacac taagacatga tagtatgtgc tcataagatc    2220
caactacgat tcgaaaccga acagaggtgc tcttattact cttatttata tttaacgtct    2280
cccccatgtt cgttatcgca gtgtgcagaa ttttcctaaa ctaattttttt ttggtattcg    2340
```

-continued

```
agatcgttga ttattagctt acaatcaaac ttccctcacc ttttccttc catcacacat    2400 ctatccacaa ttggcttggt tgcatctgat agctagctgg cggaaacatc agtcaaaaaa    2460
catgaagact actttctgag agacataagt taaagcagtt gctgaaaaat cgtcgttatc    2520
caattgataa cagaagcaac tgaagaaata aaaaattgcg catgcccgga gtcgaaccgg    2580
g                                                                  2581
```

<210> SEQ ID NO 10
<211> LENGTH: 2143
<212> TYPE: DNA
<213> ORGANISM: Artificial Sequence
<220> FEATURE:
<223> OTHER INFORMATION: Pichia pastoris Lys4 gene (incomplete)
<220> FEATURE:
<221> NAME/KEY: misc_feature
<222> LOCATION: (1245)...(1247)
<223> OTHER INFORMATION: Stop codon

<400> SEQUENCE: 10

```
atccccgtat caatgaagag actttgtccg atttgattac caacaagatg gatgctgacc      60
ccgatgctta ctacgccaaa accttaacag tagacctctc caccatgtct ccgtacatat     120
ccggaccaaa ctctgtaaag atttctaatt ctctggagga tctgtccaac aagaacatga     180
agataaacaa ggcctatttg gtctcatgta ccaattccag actgtccgac ataagggctg     240
ctgctgatgt tatcaagggt aagaaagttg ctcctggtgt cgagttttac attgcagccg     300
cctccagtga agttcagaaa gaggctgaat ctgatggttc gtggaattca ttgatcgatg     360
ccggtgctat tactttaccg gcaggttgtg gtccctgtat tggtctagga actggttgt     420 tggaagaagg cgaagttggt atttccgcta ccaacagaaa cttcaaaggt agaatggggt     480
caaaggatgc gctcgcattc ttggcttccc cagaagttgt tgcagcatct gcagtgatgg     540
gtaagattgc tggaccagaa gaagttgagg gaaacccagt aaaacgtgtc agagaccta      600 aaaagagcat aattattcac gaacctgaac aatcggaatc tgcaggagga gctgtggaag     660
ttcttgctgg tttccccgag tcgattgaag gtgagctaat tctctgtgat gctgataaca     720
tcaatactga cggtatctat ccaggaaaat acacttacca ggacgatgtt tctcgtgaaa     780
aaatggccga agtctgtatg gagaattacg acccagaatt cggaagcaaa accaaaccgg     840
gcgatattat tgtgtcaggt tataactttg aacagggtc ttcaagagag caagcggcta     900
ccgcaatctt agccagagac atgaagttga ttgtggcagg ttcctttggt aatatttttt     960
ccagaaattc cattaacaac gccttactga ctcttgagat ccctaagtta atcaacatgc    1020
taagagaaaa gtattccagt aacgaggaga aggaattgac ccgaagaact ggatggttcc    1080
tcaaatggga tgtcaaagcc gctaccgtga ctgttactga cggcaagagt ggagaagttg    1140
tcttgaaaca aaaagttgga gaattgggaa ccaatctgca agatatcatt attaaaggcg    1200
gtcttgaagg ttgggtcaag gccaaactgg cggaaaccag tacgtagagt gacattgtca    1260
caatatattt atttatttat tgatagaata gaaattcctg tatctaccta ctaatataca    1320
gagtgtttac taaaccgtcc ttccctcttt ttctctcact tacaacgagc caacttcctt    1380
gactacctcg tcgaaagaat ctttgtactc ttcggctgtt ttgctttctc ccttcttgct    1440
cttgttagca tttggaacga tcatgacaca agaagttggg cgcttggtag ctccagcaga    1500
tcccagatcc tccttagaag gtaagaacaa atatggaacg ttactatcct cacataaaac    1560
tggaatatga gaaataacat ctggtggtga aatgtcacct gcaatgatca ctaaccctt     1620 ctctcccttt cttaaggatt tcacgacctc tttaacacct cttctcacat gcttggcttt    1680
```

```
ggaagccttc ttgacagttt tgagaacctt tttgttaagc tttttagagg ctaaaggttt      1740
agcaaaaggc aaaagtgcag gcaacttctt gtcgtagttg tcttcagttt cctccttact      1800
ggcgctcttc tctttttttg acattgtttg atagttgaat tatcggaaac taaaaaaaaa      1860
tttcaactat accagcttac aaaaaaaaat ttagcactga gaacttggtc gtgtccactc      1920
tattttacta gatatttgta tcaagcttaa gtaataattt gaactaaggt cgtgcattca      1980
caactttgct ttactatctc agaaagcact acttcacttc aggaagagac ataaggtgaa      2040
catgtcttca agaaggact cttccaagag aatgtccctc ttcggaccgc tgaagggtac       2100
cggaatactt ggatttggtc acaatgacac taaacagcag cat                        2143

<210> SEQ ID NO 11
<211> LENGTH: 3340
<212> TYPE: DNA
<213> ORGANISM: Artificial Sequence
<220> FEATURE:
<223> OTHER INFORMATION: Pichia pastoris Ade2 gene (incomplete)
<220> FEATURE:
<221> NAME/KEY: misc_feature
<222> LOCATION: (1653)...(1655)
<223> OTHER INFORMATION: Stop codon

<400> SEQUENCE: 11
agctaggccg aatgattgtt gaggccgcta gcaggctcaa tatcaagacc gtgattcttg        60
atgatggttt ttcacctgct aagcacatta atgctgcgca agaccacatc gacggatcat       120
tcaaagatga ggaggctatc gccaagttag ctgccaaatg tgatgttctc actgtagaga       180
ttgagcatgt caacacagat gctctaaaga gagttcaaga cagaactgga atcaagatat       240
atcctttacc agacaatc gaactaatca aggataagta cttgccaaag gaacatttga         300
tcaagcacaa catttcggtg acaaagtctc agggtataga atctaatgaa aaggcgctgc       360
ttttgtttgg agaagagaat ggatttccat atctgttgaa gtcccggact atggcttatg       420
atggaagagg caattttgta gtggagtcta agaggacat cagtaaggca ttagaattct        480
tgaaagatcg tccattgtat gccgagaagt ttgctccttt tgttaaagaa ttagcggtaa       540
tggttgtgag atcactggaa ggcgaagtat tctcctaccc aaccgtagaa actgtgcaca       600
aggacaatat ctgtcatatt gtgtatgctc cggccagagt taatgacacc atccaaaaga       660
aagctcaaat attagctgaa aacactgtga agactttccc aggcgctgga atcttcggag       720
ttgagatgtt cctattgtct gatggagaac ttcttgtaaa tgagattgct ccaaggcccc       780
acaattctgg tcactataca atcgatgcat gtgtaacatc tcagttcgaa gcacatgtaa       840
gagccataac tggtctgcca atgccactag atttcaccaa actatctact tccaacacca       900
acgctattat gctcaatgtt ttgggtgctg aaaaatctca cggggaatta gagttttgta       960
gaagagcctt agaaacaccc ggtgcttctg tatatctgta cggaaagacc acccgattgg      1020
ctcgtaagat gggtcatatc aacataatag gatcttccat gttggaagca gaacaaaagt      1080
tagagtacat tctagaagaa tcaacccact taccatccag tactgtatca gctgacacta      1140
aaccgttggt tggagttatc atgggttcag actctgatct acctgtgatt tcgaaaggtt      1200
gcgatatttt aaaacagttt ggtgttccat tcgaagttac tattgtctct gctcatagaa      1260
caccacagag aatgaccaga tatgccttg aagccgctag tagaggtatc aaggctatca      1320
ttgcaggtgc tggtggtgct gctcatcttc caggaatggt tgctgccatg actccgttgc      1380
cagtcattgg tgttcctgtc aagggctcta cgttggatgg tgtagactcg ctacactcga      1440
ttgtccaaat gcctagaggt gttcctgtgg ctacggttgc tatcaacaac gccaccaatg      1500
```

-continued

```
ccgctctgtt ggccatcagg attttaggta caattgacca caaatggcaa aaggaaatgt    1560
ccaagtatat gaatgcaatg gagaccgaag tgttggggaa ggcatccaac ttggaatctg    1620
aagggtatga atcctatttg aagaatcgtc tttgaattta gtattgtttt ttaatagatg    1680
tatatataat agtacacgta acttatctat tccattcata attttatttt aaaggttcgg    1740
tagaaatttg tcctccaaaa agttggttag agcctggcag ttttgatagg cattattata    1800
gattgggtaa tatttacccT gcacctggag gaactttgca aagagcctca tgtgctctaa    1860
aaggatgtca gaattccaac atttcaaaat tatatctgca tgcgtctgta atactggaac    1920
tgttattttt ctggtcagga tttcaccgct cttgtcgtca tgtttctcgt cgtctgaaag    1980
taaactgact ttcctctttc cataaacaca aaaatcgatt gcaacttggt tattcttgag    2040
attgaaattt gctgtgtctt cagtgcttag ctgaatatca acaaacttac ttagtactaa    2100
taacgaagca ctatggtaag tggcataaca tagtggtatt gaagcgaaca gtggatattg    2160
aacccaagca ttggcaacat ctggctctgt tgatactgat ccggatcgtt tggcaccaat    2220
tcctgaaacg gcgtagtgcc accaaggttt cgatttgaga acaggttcat catcagagtc    2280
aaccacccca atgtcaatgg caggctccaa cgaagtaggg ccaacaacaa caggaagtat    2340
ttgaccttga agatctgttc ctttatgatc caccacacct tgccccaatt ccataacttt    2400
taccagtccc gatgcagaca tgataactgg tactaatgat ctccattgat tttcgtcggc    2460
actacgtaaa gcctccaaaa atgaattcag aatatcttct gaaactagat tctgcttctg    2520
tgattcaagc attgctttat gtagacatct cttgaataaa agcaattctc cacatattgg    2580
tgtgtgtaag atagatctgg aaagatgtat ctggaatagt ccagtcaacg ttgtgcaatt    2640
gattagcatt accttactgt gaacatctct atctacaaca acagactcaa ttcgatagac    2700
gttccgggaa agtttttcaa gcgcattcag tttgctgttg aacaaagtga ctttgctttc    2760
caatgtgcaa ataccctgt  atatcaagtc catcacatca ctcaagacct tggtggaaaa    2820
gaatgaaaca gctggagcat aattttcgaa tgaattaggt aaggtcactt catccttatc    2880
tgttgtaatg ctataatcaa tagcggaact aacatcttcc catgtaacag gtttcttgat    2940
ctctgaatct gaatctttat ttgaaaaaga attgaaaaaa gactcatcac tcattgggaa    3000
ttcaaggtca ttagggtatt ccattgttag ttctggtcta ggtttaaagg gatcaccttc    3060
gttaagacga tggaaaatag ctaatctgta caataaccag atacttctaa cgaagctctc    3120
tctatccatc agttgacgtg ttgaggatat ctgaactagc tctttccact gcgaatcagg    3180
catgctcgta tagctggcaa gcatgttatt cagctttacc aagttagaag ccctttggaa    3240
accatctata gattcccgaa aaaacttata cccactgagg gtttcactga gcatagtcag    3300
tgacatcaaa gagcatttca aatccatctc aggccagtat                          3340
```

RECOMBINANT VECTORS

CROSS REFERENCE TO RELATED APPLICATIONS

This application is the National Stage entry of PCT/US2007/012198, which was filed 18 May 2007, and which claims the benefit of U.S. Provisional Application No. 60/801,688 filed 19 May 2006.

BACKGROUND OF THE INVENTION (1) Field of the Invention

The present invention relates to the field of molecular biology, and recombinant bioengineering. In particular, the invention relates to materials and methods for integrating heterologous nucleic acids into the genome of a host organism with little or no disturbance of expression of the genes located in the integration site of the host.

(2) Description of Related Art

Recombinant bioengineering technology has enabled the ability to introduce heterologous or foreign genes into hosts and organisms to produce hosts and organisms that can then be used for the production and isolation of the proteins encoded by the heterologous genes. Numerous recombinant expression systems are available for expressing heterologous genes in mammalian cell culture, plant and insect cell culture, and microorganisms such as yeast and bacteria. However, currently available recombinant expression systems are subject to factors that can limit their utility. These factors include the stability of the transformants; the viability of the recombinantly transformed vector and hosts; and the ability to control for factors such as number of copies of the plasmid vector incorporated into a host genome.

Current methods of recombinant bioengineering for producing stable recombinant hosts commonly use so-called "knock-out" vectors in which a heterologous gene to be expressed in a host is inserted into a known locus or site within the host's genome. The "knock-out" vector consists of an expression cassette flanked by nucleic acid sequences homologous to the nucleic acid sequences flanking the site in the locus where the heterologous gene will be inserted. Typically, the flanking nucleic acid sequences are homologous to the nucleic acid sequences flanking an existing gene that is either known to encode a protein that is not essential for the host's survival or a gene whose absence may be complemented. The inserted expression cassette will replace all or part of the gene at the insertion site. The open reading frame (ORF) regions of genes are typically used as insertion loci because the nucleic acid sequences encoding ORFs are usually well-characterized in terms of structure and function. Because untranslated areas of the host genome are not well understood, insertions into those regions may have unpredictable effects on the host which may fatally or adversely affect growth of the host to such an extent as to render the host unsuitable for expressing the heterologous protein.

However, the number of loci within a host genome's coding sequences, or ORFs, known to encode for non-essential proteins may be quite limited. Additionally, once a given integration locus has been used, it is not possible to use that same locus for further integration within the host. Furthermore, because the 'knock-out' method of transformation replaces a functional unit within the host genome, there may be significant perturbation of the genome, which will eventually exhibit adverse effects on the host's productivity or viability.

A second method of constructing recombinant hosts typically involves the use of "roll-in vectors" in which an expression cassette may be inserted using a single cross-over at an insertion locus within the host genome. Because only a single site is used for integration, it is possible to use either coding sequence or non-translated sequence within the locus. If a known ORF is used for the insertion site, the "roll-in" vector may also "knock out" expression of the ORF thereby eliminating expression of the encoded protein and, therefore, will have the disadvantages enumerated above for "knock out" vectors. If a roll-in vector is designed to insert an expression cassette into an untranslated sequence locus, it is possible that minimal adverse effects on the host will be observed. However, it is also possible that the untranslated sequence locus may entail an essential function, in which case unpredictable adverse effects may occur.

The use of roll-in vectors has further disadvantages. In particular, because the roll-in vector relies upon the occurrence of only a single recombination event to integrate into the genome, it is relatively unstable, and the vector may be eliminated from the cell by further recombinant events. Also, the roll-in vector results in an unpredictable gene copy number because multiple insertions may occur either at the same or different insertion sites.

In order to extend the engineering of recombinant expression systems, and to further the development of novel expression systems such as the use of lower eukaryotic hosts to express mammalian proteins with human-like glycosylation, it is necessary to design improved methods and materials to extend the skilled artisan's ability to accomplish complex goals, such as integrating multiple genetic units into a host, with minimal disturbance of the genome of the host organism.

BRIEF SUMMARY OF THE INVENTION

The present invention provides methods and materials for producing recombinant hosts that stably express heterologous proteins in which the nucleic acids encoding the heterologous proteins are inserted anywhere within the genome of the host with minimal or no effect on expression of any of the genes at or around the insertion site. The method and vectors enable expression cassettes to be integrated into a gene of a host to make a recombinant host while preserving the function of the gene. The functional expression of the gene is not disrupted even though the expression cassette has been inserted into the gene because the vectors disclosed herein direct integration of the expression cassette into a site just outside of the ORF comprising the host gene and provide expression control sequences that enable expression of the gene to be maintained. Thus, the methods and materials of the present invention allow for the integration of heterologous nucleic acids into the genome of the host with minimal or no disturbance of function of the genome in the region in which the plasmid has been integrated.

Using the methods and vectors as disclosed herein, homologous recombination occurs in such a manner as to create intergenic regions, such that recombinant vectors encoding a number of heterologous proteins or nucleic acids can be integrated into the genome with minimal disruption to the host genome. The invention has particular utility when it is desired to integrate multiple heterologous genes into the genome of a host. The method uses a knock-in vector, which is designed to introduce an intergenic region adjacent to an ORF or coding sequence in the host genome. The intergenic region contains an expression cassette that expresses the heterologous protein. Because the expression cassette is contained within the newly created intergenic region, no ORF or coding sequence of the host is disrupted. The intergenic region is created by adding a transcriptional terminator region right after the stop codon of the ORF in the 5' crossover region of the knock-in vector. The 3' crossover region of the vector starts at the 5' end with the nucleotide that follows the stop codon of the ORF in the genome. The vector then contains an expression cassette encoding a heterologous protein, fusion protein, antisense RNA molecule, or RNAi molecule and, optionally, an expression cassette encoding a marker for selection or identification of the recombinant host. Because insertion of the nucleic acid encoding the heterologous protein minimally affects expression of the genes at or around the insertion site, the vector enables any location in the host gene to be used as an insertion site. Thus, nucleic acids encoding a heterologous protein or the like can be inserted not only into genes encoding functions non-essential for survival of the host but also into genes that encode functions that are essential for survival of the host and without the need to complement the lost function.

Thus, provided are methods and vectors for stably integrating heterologous nucleic acid sequences into a host genome without duplicating sequences or ORFs (or gene products produced from ORFs) and without deleting host sequences. Accordingly, the present invention provides a very valuable tool to the molecular biologist who wants to modify a host's genome very specifically: allowing for the targeted insertion and stable integration into the host of one or more heterologous genes, under the control of suitable regulatory sequences. The method is highly advantageous in that it allows for stable and targeted integration, in a controlled manner that reduces the likelihood that the integrated sequence will be disrupted, eliminated, or excised by further recombinant events. In addition, transformation or transfection of cells with the vectors disclosed herein results in relatively minor disruption to the host genome, so that, the cell's productivity and characteristics will be largely unaffected, other than by the effects of the gene product(s) of the heterogeneous sequences that have intentionally been incorporated therein. Furthermore, because no host sequences are lost, the method and vectors can be used for the stable and controlled transformation of organisms whose entire genomic sequence may not be known, reducing or eliminating the possibility that an essential genomic sequence will be unintentionally deleted or disrupted.

Further provided are hosts that have been stably transformed with one or more of the vectors as disclosed herein. These hosts will have stably integrated into their cellular genome one or more expression cassettes which will each direct the expression of its respective heterologous gene product. However, the hosts otherwise maintain their native genome with little or no additional disruption to the host. Such hosts may have a variety of uses, including their use for highly specific screening of the in vivo effects that the heterologous sequences have on the host. In addition, the hosts may be particularly well suited for the creation and improvement of cellular expression systems.

Thus, the methods and vectors are advantageous in that they allow the molecular biologist to very specifically transform hosts with one or more expression cassettes into the host genome in a manner which provides control of copy number, and stability of integration, while minimizing or avoiding the risk of unintentionally altering the host genome in a way that may be deleterious to the host, or may otherwise interfere with the goals of expressing the specific gene product(s) of the one or more heterologous sequences, which have been intentionally incorporated into the host genome.

Among the problems addressed by the method is the lack of sufficient loci to stably integrate foreign DNA without having to knock out or otherwise modify genes in the genome of an organism. A significant advantage is that essentially any known ORF can be used to integrate genes of interest, without affecting the expression of the gene encoded by the chosen ORF. Another significant advantage of the system is that the vectors contain an additional transcription termination sequence, such that genomic transcription in both directions is largely undisturbed by the insertion of the vectors. Another significant advantage is that it allows the integration of multiple heterologous genes via a single homologous recombination event, using a single genetic marker.

The inventors have used vectors of the present invention, which they have termed 'knock-in' vectors, or 'KINKO' (acronym for "Knock-In with little or No Knock-Out") vectors in the construction of recombinant yeast strains, particularly *Pichia pastoris*. They have been used to specifically integrate many of the genes necessary to produce glycoproteins in *P. pastoris* that have complex, mammalian N-glycan structures. To date, knock-in vectors have been constructed and used for various genomic loci of *P. pastoris*, such as the loci of auxotrophic markers URA3, HIS4, ARG4, ADE1, ADE2, HIS3, PRO1, PRO2, TRP1, TRP5, LYS1, LYS4, and THR1. However, because of their minimal disruption of the genome, the vectors have potentially universal use, and many different types of knock-in vectors can be constructed as taught herein.

Thus, the present invention provides methods and materials for the improved transformation of cells and viruses, such that said transformed cells are able to express multiple heterologous genes, with minimal or reduced disturbance of the native host genome. In certain embodiments, the present invention allows for the production of transformed hosts, such as lower eukaryotic hosts, cell lines, and organisms, with improved characteristics, namely the ability to express multiple heterologous genes involved in glycosylation, with minimal disturbance to the viability and productivity of the transformed hosts, cell lines, and organisms, such that upon further transformation with a vector encoding a desired glycoprotein, the hosts, cell lines, and organisms are able to produce such glycoprotein in a form that comprises a desired N-linked glycoform.

Thus, the present invention provides methods and materials for the improved transformation of hosts and viruses, such that said transformed hosts are able to express multiple heterologous genes, with minimal or reduced disturbance of the native host genome. In certain embodiments, the present invention allows for the production of transformed hosts, such as lower eukaryotic hosts, cell lines and organisms, with improved characteristics, namely the ability to express multiple heterologous genes involved in glycosylation, with minimal disturbance to the viability and productivity of the transformed hosts, cell lines, and organisms, such that upon further transformation with a vector encoding a desired glycoprotein, said hosts, cell lines, and organisms are able to produce such glycoprotein in a form that comprises a desired N-linked glycoform. Upon secretion and isolation of such glycoprotein, the methods and materials increase greatly the ability to obtain compositions of such glycoprotein, wherein the glycoprotein compositions comprise a desired N-linked glycoform as the predominant species thereof. In particular embodiments, the methods and materials of the invention allow the production of transformed hosts, which are able to produce glycoprotein compositions comprising predominantly a desired N-linked glycan structure selected from the group consisting of: $NANA_2Gal_2GlcNAc_2Man_3GlcNAc_2$; $Gal_2GlcNAc_2Man_3GlcNAc_2$; $GlcNAc_2Man_3GlcNAc_2$;

Man$_3$GlcNAc$_2$; NANAGalGlcNAcMan$_5$GlcNAc$_2$; GalGlcNAcMan$_5$GlcNAc$_2$; GlcNAcMan$_5$GlcNAc$_2$ and Man$_5$GlcNAc$_2$.

As discussed earlier, the method and vectors have broad application in a wide variety of expression systems, including not only lower eukaryotic systems, but also higher eukaryotic systems, such as mammalian, insect, and plant as well as prokaryotic systems. The non-limiting examples which follow describe the use of the methods and materials of the present invention which are adapted for preparation of lower eukaryotic hosts, particularly *Pichia pastoris*, containing multiple genes involved in glycosylation of glycoproteins produced by such hosts, as well as vectors useful for preparation of such hosts. However, it will be understood by one skilled in the art that the methods and materials of the invention are quite versatile and can be used, with modifications and adaptations within the means of the skilled artisan, for the construction of hosts and vectors for additional purposes. Such modifications, adaptations and usages can be accomplished without variance from the spirit and practice of the present description, and are therefore considered to be within the scope of the invention.

DEFINITIONS

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply, "expression vectors").

As used herein, the term "sequence of interest" or "gene of interest" refers to a nucleic acid sequence, typically encoding a protein, antisense molecule, or RNAi molecule, that is not normally produced in the host cell. The methods disclosed herein allow one or more sequences of interest or genes of interest to be stably integrated into a host cell genome. Non-limiting examples of sequences of interest include sequences encoding one or more polypeptides having an enzymatic activity, e.g., an enzyme which affects N-glycan synthesis in a host such as mannosyltransferases, N-acetylglucosaminyltransferases, UDP-N-acetylglucosamine transporters, galactosyltransferases, UDP-N-acetylgalactosyltransferase, sialyltransferases, and fucosyltransferases.

The term "gene" refers to a transcription unit comprising an open reading frame operably linked to expression control sequences.

The term "operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "marker sequence" or "marker gene" refers to a nucleic acid sequence capable of expressing an activity that allows either positive or negative selection for the presence or absence of the sequence within a host cell. For example, the *P. pastoris* URA5 gene is a marker gene because its presence can be selected for by the ability of cells containing the gene to grow in the absence of uracil (See U.S. Pub. Application No. 20040229306). Its presence can also be selected against by the inability of cells containing the gene to grow in the presence of 5-FOA. Marker sequences or genes do not necessarily need to display both positive and negative selectability. Non-limiting examples of marker sequences or genes from *P. pastoris* include ADE1, ARG4, HIS4 and URA3. For antibiotic resistance marker genes, kanamycin, neomycin, geneticin (or G418), paromomycin and hygromycin resistance genes are commonly used to allow for growth in the presence of these antibiotics.

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "eukaryotic" refers to a nucleated cell or organism, and includes insect cells, plant cells, mammalian cells, animal cells and lower eukaryotic cells.

The term "lower eukaryotic cells" includes yeast, fungi, collar-flagellates, microsporidia, alveolates (e.g., dinoflagellates), stramenopiles (e.g., brown algae, protozoa), rhodophyta (e.g., red algae), plants (e.g., green algae, plant cells, moss) and other protists. Yeast and fungi include, but are not limited to: *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium luc-* knowense, Fusariunm sp., Fusarium gramineum, Fusarium venenatum, Physcomitrella patens and Neurospora crassa. Pichia sp., any Saccharomyces sp., Hansenula polymorpha, any Kluyveromyces sp., Candida albicans, any Aspergillus sp., Trichoderma reesei, Chrysosporium lucknowense, any Fusarium sp. and Neurospora crassa.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins of the present invention have particular utility. The heterologous polypeptide included within the fusion protein of the present invention is at least 6 amino acids in length, often at least 8 amino acids in length, and usefully at least 15, 20, and 25 amino acids in length. Fusions also include larger polypeptides, or even entire proteins, such as the green fluorescent protein ("GFP") chromophore-containing proteins having particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

DETAILED DESCRIPTION OF THE INVENTION

Figure 1:
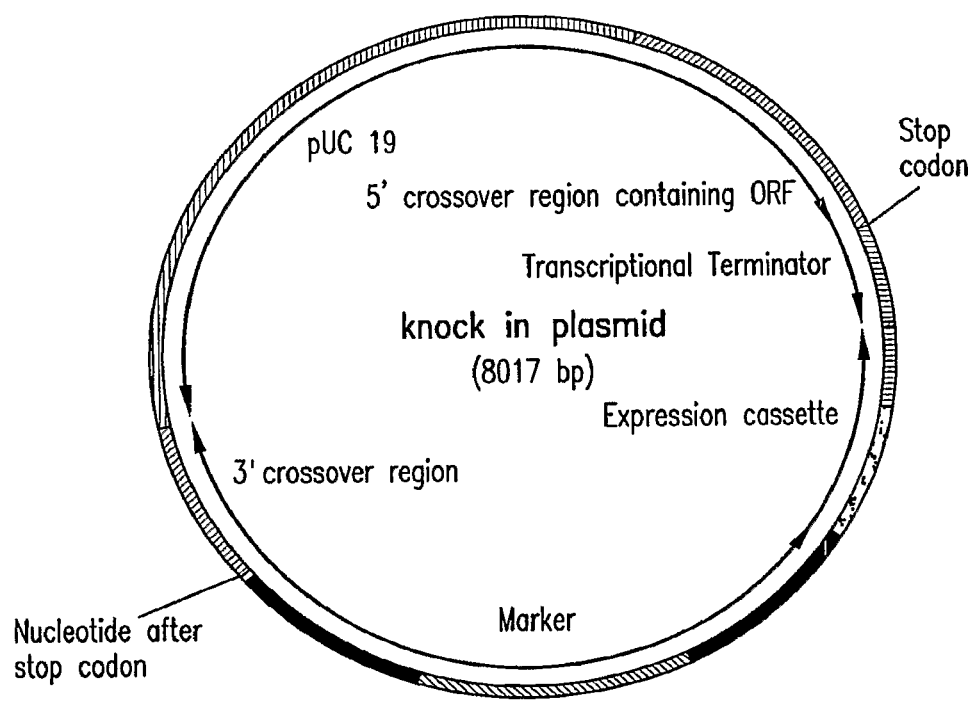
FIG. 1 shows the typical structure of an embodiment of the knock-in vector showing the 5' crossover region containing an ORF, the adjacent transcription terminator sequence, an expression cassette, an expression cassette encoding a marker gene, and 3' crossover region. The position of the expression cassette and marker expression cassette relative to each other can be varied as well as the orientation. The stop codon of the ORF in the 5' crossover region and the first nucleotide following the ORF in the 3' crossover region are indicated.

The present invention provides methods and materials for producing recombinant hosts that stably express a heterologous sequence of interest in which the sequence of interest can be inserted anywhere within the genome of the host with minimal or no effect on expression of any of the genes at or around the insertion site. Thus, the methods and materials of the present invention allow for the integration of heterologous nucleic acids into the genome of the host with minimal or no disturbance of function of the genome in the region in which the plasmid has been integrated.

The method uses a knock-in vector, which is designed to introduce an intergenic region adjacent to an ORF or coding sequence in the host genome. The intergenic region contains on or more expression cassettes, each expressing a sequence of interest. Because the one or more expression cassettes are contained within the newly created intergenic region, no ORF or coding sequence of the host is disrupted. The intergenic region is created by adding a transcriptional terminator region right after the stop codon of the ORF in the 5' crossover region of the knock-in vector and the 3' crossover region of the vector starts at the 5' end with the nucleotide that follows the stop codon of the ORF in the genome or the intergenic region is created by adding a promoter right before the start codon of the ORF in the 3' crossover region of the knock-in vector. The vector then contains one or more expression cassettes, each containing a sequence of interest, which can encode for example, a heterologous protein, fusion protein, antisense molecule, or RNAi molecule and, optionally, a second expression cassette encoding a detectable or selectable marker for facilitating selection or identification of the recombinant host (See, for example, FIGS. 1-3). Examples of detectable or selectable markers include, but are not limited to, genes encoding antibiotic resistance; genes encoding proteins that complement the absence of the protein in the host; genes encoding enzymatic activities such as beta-galactosidase; green fluorescent protein; and genes encoding proteins detectable using antibodies or the like. Because insertion of the expression cassettes minimally affects expression of the genes at or around the insertion site, the vector enables any location in the host gene to be used as an insertion site. Thus, expression cassettes can be inserted not only into genes encoding functions non-essential for survival of the host but also into genes that encode functions that are essential for survival of the host and without the need to complement the lost function.

Thus, what is provided is a polynucleotide construct or vector adapted to integrate into a target polynucleotide by recombination, the construct comprising: (a) a first and second nucleotide sequence each homologous with a corresponding nucleotide sequence flanking a desired integration site in a target polynucleotide, the first and second nucleotide sequences being capable of undergoing homologous recombination with the corresponding nucleotide sequence flanking the desired integration site; (b) a third nucleotide sequence operably linked to the first and second nucleotide sequences, the third nucleotide sequence comprising one or more expression cassettes and the third nucleotide sequence being situated in a region of the construct located between the first and second nucleotide sequences so as to enable the third nucleotide sequence to become integrated into the target polynucleotide whenever the polynucleotide construct homologously recombines with the target polynucleotide; and (c) a fourth nucleotide sequence operably linked to the first and third nucleotide sequences or the second and third nucleotide sequences, wherein the fourth nucleotide sequence includes an expression control sequence and is located between the first and third nucleotide sequences or third and second nucleotide sequences. In further embodiments, the third nucleotide sequence includes at least two expression cassettes and one of the expression cassettes encodes a detectable or selectable marker.

In particular embodiments of the vector, the first nucleotide sequence comprises an ORF, which ends at the 3' end of the first nucleotide sequence, the fourth nucleotide sequence is located between the first and third nucleotide sequences, and the fourth nucleotide sequence comprises a transcription termination sequence capable of terminating transcription of the ORF when the construct is integrated into the genome of a host. In other embodiments of the vector, the second nucleotide sequence comprises an ORF, which begins at the 5' end of the second nucleotide sequence, the fourth nucleotide sequence is located between the third and second nucleotide sequences, and the fourth nucleotide sequence comprises a promoter sequence capable of initiating transcription of the ORF when the construct is integrated into the genome of a host.

FIG. 1 illustrates the design of a typical knock-in plasmid vector for integrating an expression cassette into the genome of a host. The orientation of the expression cassettes relative to each other and to the ORF can be in either direction. While FIG. 1 shows the expression cassette following the transcription termination sequence adjacent to the ORF stop codon, in other embodiments the marker expression cassette can follow the transcription termination sequence adjacent to the ORF stop codon. While FIG. 1 shows one expression cassette comprising a sequence of interest and one expression cassette encoding a detectable marker, in further embodiments, the vector can contain a plurality of expression cassettes. Each sequence of interest can have its own promoter and terminator. In addition or alternatively, polycistronic vectors may be used in which expression of more than sequences of interest, each with its own initiator and stop codons, are driven by a single promoter and terminator sequence. As shown in FIG. 1, the marker is a second expression cassette that can have its own promoter and termination sequence. In particular embodiments, the most 3' expression cassette can use the transcription termination sequences in the 3' flanking crossover region.

Figure 2A:
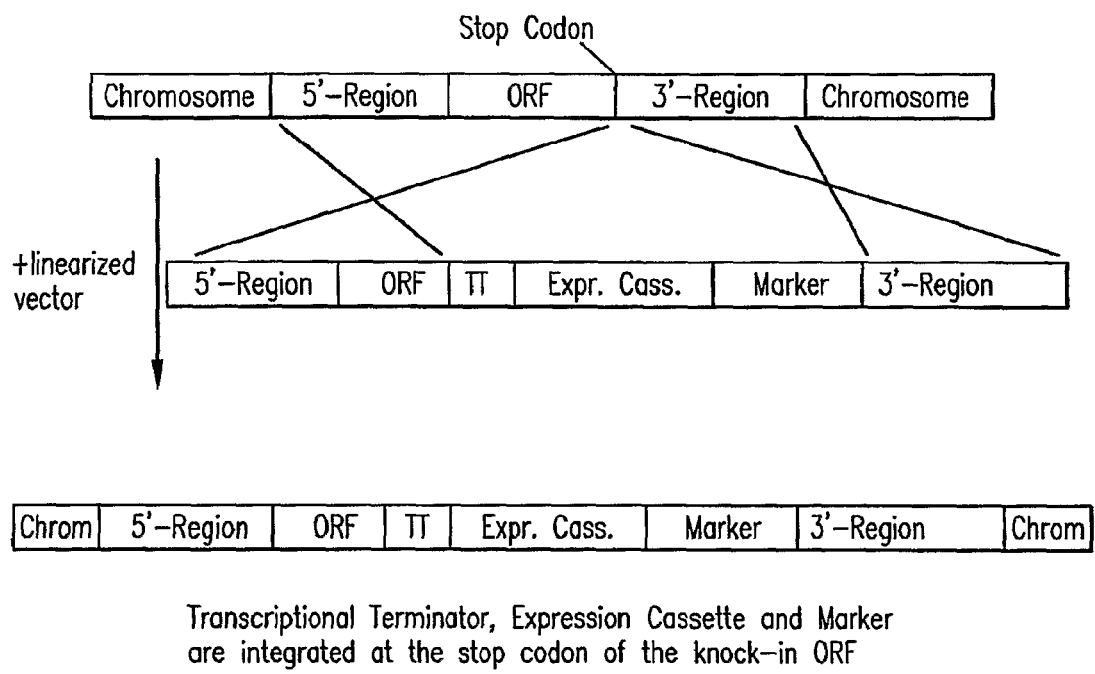
FIG. 2A illustrates how the embodiment of the knock-in vector shown in FIG. 1 is inserted into the genome downstream of the stop codon of the endogenous ORF by homologous recombination. ORF—Open Reading Frame. TT—Heterologous transcription terminator sequence. The 3' region of the expression cassette contains its own transcriptional termination sequence. Expr. Cass.—Expression Cassette. For homologous recombination, the 5'-region, ORF and 3'-region are homologous to genomic sequences in the host.

FIG. 2A illustrates how the expression cassette is integrated into genome of the host by homologous recombination. The Figure shows an ORF in the genome of a host with 5' and 3' flanking crossover sequences. The stop codon of the ORF in the 5' flanking crossover region is indicated. The knock-in vector is preferably linear or linearized and is shown below the integration region of the host genome. As shown, the vector contains the 5' and 3' flanking crossover regions and the ORF. However, adjacent to and 3' of the stop codon in the ORF is a heterologous transcription terminator sequence, which will cause termination of transcription of the ORF and thus enable a functional RNA transcript of the ORF to be transcribed and translated. Adjacent to and 3' of the heterologous transcription terminator sequence is an expression cassette comprising a transcription unit, which encodes, for example, a heterologous protein, fusion protein, antisense molecule, RNAi molecule, or the like. In general, in most embodiments, the expression cassette comprises a promoter, an ORF, and a transcription termination sequence. The orientation of the expression cassette relative to the ORF can be in either direction. Adjacent to the expression cassette as shown in the Figure can be an expression cassette encoding a detectable marker for facilitating selection or identification of a recombinant host comprising the integrated sequences. Orientation of the expression cassette encoding the detectable marker relative to the ORF can be in either direction. Adjacent to, and 3' of the expression cassette encoding the marker, is a 3' flanking region. In lieu of providing a transcription termination sequence for this 3' expression cassette, the transcription termination sequence contained within the 3' flanking crossover region can be used.

Also shown in FIG. 2A is the genome after the vector has been integrated into the genome by homologous recombination via the 5' and 3' flanking sequences. As shown, transcription of the ORF will terminate in the heterologous transcription termination sequence following the ORF, producing an RNA transcript similar in function to the RNA transcript produced in the non-recombinant host. Thus, the function encoded by the ORF has not been disrupted because the transcript will produce a functional gene product encoded by the ORF just like in the non-recombinant host. Therefore, because the integrated sequences do not disrupt functional gene expression (that is, allows production of a functional transcript of the gene it is inserted into that can be translated into a functional gene product) if the ORF encodes an essential gene product, that gene product will continue to be made in the recombinant host. However, unlike the non-recombinant host, the recombinant host now includes the expression cassettes and will express the proteins or RNA encoded by the expression cassettes. It is important to note that 3' flanking region remains intact as in the non-recombinant host. Therefore, all 3' flanking functions remain functional, for example, regulatory sequences for controlling expression of the genes downstream of the integration site.

While FIGS. 1 and 2A and B show vectors having a detectable and selectable marker in addition to an expression cassette, in particular embodiments the vectors contain one or more expression cassettes encoding sequences of interest but do not contain an expression cassette encoding a detectable or selectable marker. The Applicants discovered that inserting the vectors disclosed herein into a host that has a mutation in the gene at the insertion locus that renders the host deficient in the product encoded by the gene at the insertion locus, results in a recombinant host that is no longer deficient in the product encoded by the gene at the insertion locus. Thus, repair of a mutation in the gene at the insertion site can serve as the selection marker. For example, if the gene at the insertion site encodes an essential gene product that can be complemented by supplementing the growth conditions with the gene product or a metabolite that complements the loss of the gene product, recombinant hosts can be identified by growing the recombinant under conditions that lack the gene product or the metabolite that complements the loss of the gene function because only recombinant hosts in which the mutated gene has been repaired will grow. Therefore, the vectors disclosed herein further include embodiments wherein the 5' or 3' flanking sequences include an ORF which can be used as a selectable marker.

Therefore, in a further embodiment, a vector is provided, which stably integrates heterologous nucleic acid sequences into a host genome without duplicating or deleting host genomic sequences. In general, the vector has the following arrangement, from the 5' to 3' direction: (a) 5' flanking sequence homologous to the 5' side of an insertion site in a target sequence in the host genome, which includes an open reading frame (ORF); (b) a first transcription termination sequence; (c) one or more expression cassettes wherein each expression cassette comprises (i) a promoter sequence; (ii) a sequence of interest; and (iii) optionally, a second transcription termination sequence; and (d) a 3' flanking sequence homologous to the 3' side of the insertion site of the target sequence. In particular embodiments, at least one of the expression cassettes encodes a detectable or selectable marker.

In a currently preferred embodiment, the 5' flanking sequence of the vector (a) includes all or part of an open reading frame (ORF) corresponding to an ORF in the host, which is operably linked with the first transcription termination sequence at the 3' end of the ORF such that the first transcription termination sequence is adjacent to the stop codon for the ORF. The ORF is preferably that of the genetic loci to which the flanking sequences are directed. In this manner, the ORF contained within the 5' flanking sequence will replace the native ORF, which is disrupted, and will be expressed under the control of the native promoter, and the first transcription termination sequence (b) of the inserted vector. The first transcription termination sequence is heterologous with respect to the ORF.

Thus, further provided is a vector for inserting a sequence of interest into a target DNA sequence in the genome of a host comprising (a) a first homologous vector DNA sequence capable of homologous recombination with a first region of the target DNA sequence, which ends at its 3' end with the stop codon of an open reading frame (ORF); (b) a heterologous transcription termination sequence operably linked to the ORF; (c) one or more expression cassettes; and (d) a second homologous vector DNA sequence capable of homologous recombination with a second region of the target DNA sequence; wherein the 5'-3' orientation of the first homologous vector sequence relative to said second homologous vector sequence is the same as the 5'-3' orientation of the first region relative to the second region of the target sequence and the first and second vector sequences correspond to adjacent first and second regions in the target DNA sequence; and wherein the vector is capable of undergoing homologous recombination with the target DNA sequence. In currently preferred embodiments, the vector has at least two expression cassettes and one of the expression cassettes encodes a detectable or selectable marker. In particular embodiments, (a) and (d) each may comprise one or more restriction sites.

Although not essential, one skilled in the art will recognize that propagation and use of the vectors herein may be enhanced by inclusion of one or more restriction sites at selected points within the vector, particularly between individual elements of the vectors, and/or at either or both ends of the flanking regions. The selected points may optimally include, for example: 5' of (a); between (a) and (b); between (b) and (c); between (c) and (d); and at the 3' end of (d). Depending upon preference for versatility, restriction sites may be paired to allow for maximal versatility of the vectors. For example, pairing a given restriction site 5' of (a) and 3' of (d) allows for ligation and removal of the entire intact vector. Pairing of a given restriction site between (b) and (c) and between (c) and (d) allows for ligation, removal, and interchanging of expression cassettes. It may also be desired to have one or more restriction sites within the first expression cassette and/or the second expression cassette, which allows for ease of interchangeably "swapping out" one or more of the components of the first and second expression cassettes to create additional expression cassettes.

In order to reduce the likelihood of an undesired cleavage, ligation, or rearrangement occurring, it is currently preferred that the restriction enzymes used be strongly site-specific; that is, that the restriction enzymes correspond to relatively rare restriction sites, which reduces the chances that an unexpected restriction site will appear within the genome. Examples of strongly site-specific restriction enzymes corresponding to relatively rare restriction sites include, but are not limited to, NotI, SfiI; RsrII; SgfI; and PacI. If desired, other convenient restriction enzymes may also be included, such as AscI; BamHI; XhoI; and BglII.

In the event that the gene in the expression cassette is intended to be secreted from the cell, or targeted to a specific location within the cell, such as the endoplasmic reticulum or the Golgi apparatus, the expression cassette may further comprise a signal sequence encoding a signal peptide, located between the expression control or promoter sequence and the sequence encoding the gene. The signal peptide is chosen for its ability to target the adjacent peptide sequence to the intended site.

The 5' and 3' flanking sequences are each complementary to a region, preferably to very close or adjoining regions, within the host genome of the intended host. For example, if the intended host is *Saccharomyces cerevisiae* or *Pichia pastoris*, the flanking sequences preferably originate from such lower eukaryotic cell. In the case of *Saccharomyces* and *Pichia*, some genetic loci for the flanking sequences for the vectors include, but are not limited to, HIS4, ARG4, ADE1, ADE2, HIS3, PRO1, PRO2, TRP1, TRP2, TRP5, LYS1, LYS4, and THR1.

Any one of the aforementioned genetic loci can also be used as selectable markers when the host to receive the vector is deficient in gene product encoded by any one of the aforementioned genetic loci. Thus, the vector can comprise an expression cassette encoding the product of one of the aforementioned loci as a marker that complements the loss of the product when the vector is inserted into a second locus of a host deficient in the gene product encoded by the marker. The vector can include the gene of a locus at the insertion locus in the 5' or 3' flanking sequences such that when the vector is inserted into the locus of a host deficient in the gene product by homologous recombination, the gene at the locus is repaired such that a functional gene product is produced at the locus.

In further embodiments, the selectable marker is counter-selectable, such that after transformation, the detectable marker can then be excised from the host genome, and by selecting for the absence of the selectable marker, a host is identified which has the expression cassette encoding the functional sequence of interest, but not the expression cassette encoding the detectable marker. Examples of currently preferred counter-selectable markers for the *Saccharomyces* or *Pichia* hosts include URA3 and URA5. In further embodiments, at least one unique restriction site is present between the first expression cassette (d) and the second expression cassette encoding the selectable marker.

In a further embodiment, the vectors of the invention comprise the following elements in the following arrangement, from the 5' to 3' direction: (a) a 5' flanking sequence homologous to the 5' side of an insertion site in a target sequence in the host genome, which includes sequence up to an open reading frame (ORF); (b) one or more expression cassettes wherein each expression cassette comprises (i) a promoter sequence; (ii) a sequence of interest; and (iii) optionally, a second transcription termination sequence; (c) a promoter sequence for regulating expression of the ORF; and (d) a 3' flanking sequence homologous to the 3' side of the insertion site in the target sequence in the host genome, which includes the ORF and its start codon.

Figure 2B:
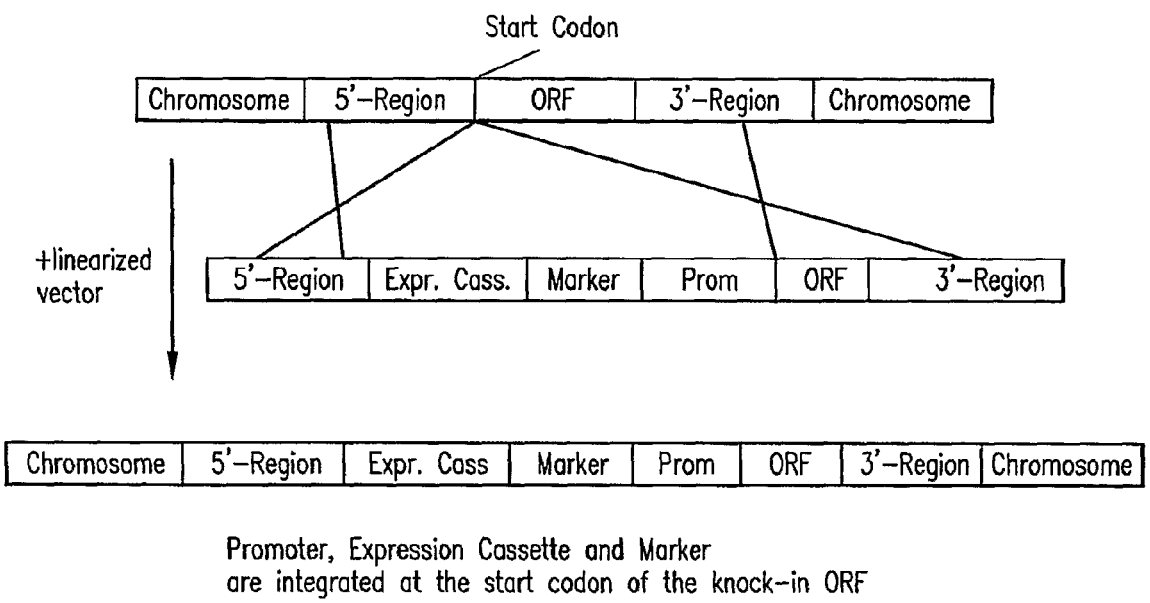
FIG. 2B illustrates how another embodiment of the knock-in vector is inserted into the genome upstream of the start codon of the endogenous ORF by homologous recombination. ORF—Open Reading Frame. Prom—Heterologous promoter sequence. The 3' region of the expression cassette contains its own transcriptional termination sequence. Expr. Cass.—Expression Cassette. For homologous recombination, the 5'-region, ORF and 3'-region are homologous to genomic sequences in the host.

In the further embodiment, the 3' flanking sequence (d) preferably includes an open reading frame (ORF) corresponding to an ORF present in the host, which is operably linked with the promoter sequence in (c). In currently preferred embodiments, the promoter (c) is a heterologous promoter with respect to the ORF. The ORF is preferably that of the genetic loci to which the flanking sequences are directed. In this manner, the ORF contained within the 3' flanking sequence will replace the native ORF, which is disrupted, and will be expressed under the control of the promoter sequence (c) of the inserted vector and the native transcription termination sequence of the disrupted ORF. The alternative embodiment is illustrated in FIG. 2B.

A further still embodiment of the vector for inserting a sequence of interest into a target DNA sequence in the genome of a host comprises (a) a first homologous vector DNA sequence capable of homologous recombination with a first region of the target DNA sequence; (b) one or more expression cassettes; (c) a promoter sequence; and (d) a second homologous vector DNA sequence capable of homologous recombination with a second region of the target DNA sequence, which begins with the start codon of an open reading frame (ORF) at its 5' end and which is operably linked to the promoter; wherein the 5'-3' orientation of the first homologous vector sequence relative to said second homologous vector sequence is the same as the 5'-3' orientation of the first region relative to the second region of the target sequence and the first and second vector sequences correspond to adjacent first and second regions in the target DNA sequence; and wherein the vector is capable of undergoing homologous recombination with the target DNA sequence.

In all other aspects, the above embodiments may be modified in accordance with the principles described with respect to the embodiments described earlier.

In certain embodiments the vectors of the present invention may have multiple expression cassettes in series within the 5' and 3' flanking sequences. In such embodiments, each expression cassette comprises a promoter, a transcription unit, and terminator sequence, such that, upon integration into the host genome, each expression cassette will operatively express its respective transcription unit under the control of its respective promoter and transcription terminator sequences. In such a manner, expression of multiple transcription units (or genes) in a host can be accomplished via a single integration event using the vectors disclosed herein. Many variations of expression cassette design are possible and their uses are within the scope of the present invention. For example, if desired, expression cassettes may be designed with multiple promoters in order to obtain stronger expression of its respective ORF, or multiple transcription units may be contained within an expression cassette under the control of one or more promoters to attain coordinated expression of multiple genes.

In the examples below, use of the vectors disclosed herein is illustrated with respect to a method for engineering lower eukaryotic hosts of the species *Pichia pastoris* so that the hosts are able to produce glycoproteins with a glycosylation pattern similar to that produced by mammalian cells. Accordingly, various components of the present invention, as described in the examples, have been optimized with respect to these particular embodiments of the invention. However, the skilled artisan will recognize the versatility of the present invention, and will recognize that the description of such optimized embodiments in no way limits the applicability of the present invention with respect to other expression systems.

Examples of promoters that are operable in *Pichia* include, but are not limited to, *Pichia* GAPDH promoters; *Saccharomyces* GAPDH promoters; *Pichia* PMA1 promoters; *Pichia* TEF promoters; *Pichia* AOX promoters; ALG6 promoters; and *Pichia* MLS1 promoters. Examples of transcription terminator sequences that are operable in *Pichia* include, but are not limited to, ALG3 terminators; *Pichia* ALG6 terminators; *Saccharomyces* cytochrome C (CYC) terminators; *Pichia* PMA1 terminators; and *Pichia* TEF terminator sequences. Examples of selectable markers for use in *Pichia* include but are not limited to, *Pichia* URA5 genes; *Pichia* URA3 genes; *Pichia* HIS (including HIS1 through HIS6) genes; and *Pichia* ARG (including ARG1 through ARG3) genes. Examples of insertion sites include, but are not limited to, *Pichia* ADE genes; *Pichia* TRP (including TRP1 through TRP2) genes; *Pichia* MCA genes; *Pichia* CYM genes; *Pichia* PEP genes; *Pichia* PRB genes; and *Pichia* LEU genes. The *Pichia* ADE1 and ARG4 genes have been described in Lin Cereghino et al., Gene 263:159-169 (2001) and U.S. Pat. No. 4,818,700, the HIS3 and TRP1 genes have been described in Cosano et al., Yeast 14:861-867 (1998), HIS4 has been described in GenBank Accession No. X56180.

The examples illustrate the practice of the present invention in currently preferred embodiments in *Pichia pastoris*. However, this invention may be applied to a wide range of host cells and expression systems using publicly available genomic databases, as well as proprietary genomic databases, which may be purchased. With recent advances in genomics sciences, the entire or partial genomes of many species are now available through the internet, or through scientific publications. (See, for example, the website of the Encyclopedia of Bioscience at Frontiers in Bioscience, PO Box 160 Albertson, N.Y. 11507-0160, which provides links to genomic databases of numerous vertebrates, insects, fungal, bacterial, and plants. See also, the genomic database services and products of Integrated Genomics, Inc. (2201 W Campbell Park DR Ste 15 Chicago, Ill. 60612), including databases for numerous microorganisms.

While the present invention is exemplified below using a *Pichia pastoris* expression system for the production of glycoproteins having fully complex sialylated N-linked glycoforms, the example is non-limiting, and the invention has much broader applicability. The skilled artisan will recognize that many modifications and improvements are possible without deviating from practicing the essence of the invention, and with such modifications, the invention may be used with virtually any type of expression system, host organism or cell. Thus, this invention may be applied to a wide range of host cells and expression systems using publicly available genomic databases, as well as proprietary genomic databases, which may be purchased for identification of target sequences and ORFs which are suitable for inserting expression cassettes as taught herein. With recent advances in genomics sciences, the entire or partial genomes of many species are now available through the internet, or through scientific publications. (See, for example, the website of the Encyclopedia of Bioscience at Frontiers in Bioscience, P.O. Box 160 Albertson, N.Y. 11507-0160, which provides links to genomic databases of numerous vertebrates, insects, fungal, bacterial, and plants. See also, the genomic database services and products of Integrated Genomics, Inc. (2201 W. Campbell Park DR, Ste. 15, Chicago, Ill. 60612), including databases for numerous microorganisms, including *Pichia pastoris*. Further, while the present invention is exemplified expressing recombinant glycoproteins with fully complex sialylated N-glycans from a *P. pastoris* expression system, many other potential applications and uses are possible as will be readily appreciated and within reach when this specification is read by the skilled artisan. Such modifications, improvements, applications and uses are within the contemplated scope of the present invention.

Example 1

In accordance with the principles, methods and materials described above, the inventors have constructed several series of vectors with the same overall architecture, but with variations designed to further elucidate the operation and optimization of the present invention.

In the first series of vectors, the inventors modified vector pJN267, the construction of which is described in U.S. Published Patent Application No. 2004/0229306 and Nett and Gemgross, Yeast 20: 1279-1290 (2003). The pJN267 vector contains the ORF encoding the *P. pastoris* URA5 gene. An AOX1 transcription termination sequence is inserted after the KEX1-5' region to generate pJN473, which is used as the master plasmid to generate the first series vectors. Note that pJN473 is not itself a vector within the present invention because of the choice of the 5' region, which is designed to knock out KEX1. Plasmid pJN473 was modified to generate two sets of vectors within the present invention, the first set of vectors using the *Pichia pastoris* URA3 blaster as the selectable marker and the second set using the *Pichia pastoris* URA5 blaster as the selectable marker.

As shown in Table 1, the 5' and 3' flanking KEX1 regions of pJN473 were excised and replaced with 5' and 3' flanking ADE1, ARG4, HIS3, HIS4, or TRP1 regions to produce vectors pJN492-496, respectively. The 5' flanking region contained the ADE1, ARG4, HIS3, HIS4, or TRP1 ORF up to the stop codon and the 3' flanking region contained the sequences downstream from the ORF, e.g., the native transcription termination sequences. These plasmid vectors then contain the AOX1 transcription termination sequence adjacent to the stop codon of the ORF and *S. cerevisiae* URA3 blaster as the selectable marker.

TABLE 1

| Plasmid | Restriction sites | 5' Flanking Region | Resulting plasmid | Restriction sites | 3' Flanking Region | Resulting plasmid |
|---|---|---|---|---|---|---|
| pJN473 | SacI/PmeI | ADE1-5' | pJN486 | SwaI/SalI | ADE1-3' | pJN492 |
| pJN473 | EcoRI/PmeI | ARG4-5' | pJN487 | SwaI/SphI | ARG4-3' | pJN493 |
| pJN473 | SacI/PmeI | HIS3-5' | pJN488 | SwaI/SalI | HIS3-3' | pJN494 |
| pJN473 | SacI/PmeI | HIS4-5' | pJN489 | SwaI/SphI | HIS4-3' | pJN495 |
| pJN473 | SacI/PmeI | TRP1-5' | pJN490 | SwaI/SalI | TRP1-3' | pJN496 |

The plasmids pJN492 to pJN496 shown in Table 1) were then modified further to contain different selectable markers. For all vectors, the *S. cerevisiae* URA3 blaster was cut out using SwaI/XhoI and the resulting ends were blunt ended using T4 DNA polymerase. Then, a DNA fragment containing the *P. pastoris* URA5 blaster was removed from plasmid pJN396 (See U.S. Pat. Pub. 2004/0229306) by digesting with EcoRI and SphI. The ends were blunt ended with T4 DNA polymerase and the fragment was inserted into plasmids pJN492 to pJN49[6] to yield plasmids pJN507a/b to pJN511a/b, respectively.

To generate another set of plasmids containing the *P. pastoris* URA3 blaster as selectable marker, plasmids pJN492 to pJN496 were modified as follows. For all vectors the *S. cerevisiae* URA3 blaster was cut out using SwaI/XhoI and the resulting ends were blunt ended using T4 DNA polymerase. Then, a DNA fragment containing the *P. pastoris* URA3 blaster was removed from plasmid pJN315 (See U.S. Pat. Pub. 2004/0229306) by digesting with SwaI and XhoI. The ends were blunt ended with T4 DNA polymerase and the fragment containing the *P. pastoris* URA3 blaster was inserted into plasmids pJN492 to pJN496 to yield plasmids pJN513a/b to pJN517a/b, respectively.

A similar set of vectors was constructed using the *P. pastoris* ALG3 (PpALG3) terminator region instead of the AOX1 terminator. PpALG3 gene has been described in Davidson et al, Glycobiol. 14: 399-407 (2004), GenBank Accession No. AY653304, and U.S. Published Patent Application No. 2005/0170452. Vector construction started with pGLY24, the master knock out plasmid, marked with the *Pichia pastoris* URA5 blaster auxotrophic marker. Plasmid pGLY24 is basically the same as p267 except with ARG3 in place of the KEX1 as the place holder. Addition of the PpALG3 terminator in the restriction site following the 5'-region resulted in the master plasmid pGLY566. Again, because of the choice of the 5' region, this vector is itself not a KINKO vector but an ARG3 knock out vector. Exchange of the 5'- and 3'-regions then resulted in the following plasmids shown in Table 2. Note: plasmid pGLY962 corresponds to pGLY566 with a destroyed BamHI site.

TABLE 2

| Plasmid | Region exchanged | Resulting plasmid | Region exchanged | Resulting plasmid |
| --- | --- | --- | --- | --- |
| pGLY566 | HIS3-5' | pGLY575 | HIS3-3' | pGLY579 |
| pGLY566 | TRP1-5' | pGLY576 | TRP1-3' | pGLY580 |
| pGLY566 | ADE1-5' | pGLY577 | ADE1-3' | pGLY581 |
| pGLY566 | ADE2-3' | pGLY1079 | ADE2-5' | pGLY1080 |
| pGLY566 | LYS4-3' | pGLY2521 | LYS4-5' | pGLY2529 |
| pGLY566 | LYS1-5' | pGLY2522 | LYS1-3' | pGLY2530 |
| pGLY566 | PRO1-5' | pGFI163 | PRO1-3' | pGFI164 |
| pGLY566-pGLY962 | TRP2-5' | pGLY971 | TRP2-3' | pGLY972 |

To test the integration efficiency of the KINKO plasmids, expression cassettes containing DNA encoding two leader/α-1,2-mannosidase fusion proteins (BC1 and BC18) were cloned into pJN507a/b to pJN511a/b and pJN513a/b to pJN517a/b and each set of plasmids was transformed into two URA5-yeast strains: strains YJN199-1 and YJN199-6 (See U.S. Published Patent Application No. 2004/0229306) for pJN507a/b to pJN511a/b (Table 3) and strains YJN227-1 and YJN227-4 (URA3-) for pJN513a/b to pJN517a/b (Table 4).

PCR analysis was performed on 48 clones per transformation. The PCR analysis showed a high level of integration efficiency into the correct locus at the correct position.

TABLE 3

| Strain | Marker | Mannosidase | pJN507a/b | pJN508a/b | pJN509a/b | pJN510a/b | pJN511a/b |
| --- | --- | --- | --- | --- | --- | --- | --- |
| YJN199-1 | PpURA5 | BC1 | 47/48 = 98% | 46/48 = 96% | 47/48 = 98% | 46/48 = 96% | 47/48 = 98% |
| YJN199-1 | PpURA5 | BC18 | 48/48 = 100% | 48/48 = 100% | 48/48 = 100% | 26/48 = 54% | 47/48 = 98% |
| YJN199-6 | PpURA5 | BC1 | 46/48 = 96% | 43/48 = 90% | 47/48 = 98% | 39/48 = 81% | 46/48 = 96% |
| YJN199-6 | PpURA5 | BC18 | 46/48 = 96% | 41/48 = 85% | 48/48 = 100% | 5/48 = 10% | 48/48 = 100% |
| | | Average | 98% | 93% | 99% | 60% | 98% |

TABLE 4

| Strain | Marker | Mannosidase | pJN513a/b | pJN514a/b | pJN515a/b | pJN516a/b | pJN517a/b |
| --- | --- | --- | --- | --- | --- | --- | --- |
| YJN227-1 | PpURA3 | BC1 | 47/48 = 98% | 30/48 = 63% | 35/48 = 73% | 33/33 = 100% | 36/48 = 75% |
| YJN227-1 | PpURA3 | BC18 | 47/48 = 98% | 42/48 = 88% | 41/48 = 85% | 34/34 = 100% | 46/48 = 96% |
| YJN227-4 | PpURA3 | BC1 | 47/48 = 98% | 85/96 = 89% | 44/48 = 92% | 31/31 = 100% | 44/48 = 92% |
| YJN227-4 | PpURA3 | BC18 | 47/48 = 98% | [contaminated] | 46/48 = 96% | 31/31 = 100% | 45/48 = 94% |
| | | Avg: | 98% | 82% | 87% | 100% | 89% |

Example 2

This example illustrates the construction of a recombinant yeast capable of producing glycoproteins having complex, mammalian-like N-glycans. A KINKO expression vector containing the five genes necessary for constructing a sialylation pathway in yeast was used to insert the five genes adjacent to the TRP2 ORF.

Methods and Materials:

Strains, culture conditions, and reagents. *Escherichia coli* strains TOP10 or XL10-Gold were used for recombinant DNA work. PNGase-F, sialidase, restriction and modification enzymes were obtained from New England BioLabs (Beverly, Mass.), and used as directed by the manufacturer. Oligonucleotides were obtained from Integrated DNA Technologies (Coralville, Iowa). Codon-optimization of genes was provided by GeneArt (Regensburg, Germany), using the GENEOPTIMIZER software adapted for *Pichia pastoris* codon usage. Metal chelating "HisBind" resin was obtained from Novagen (Madison, Wis.). 96-well lysate-clearing plates were from Promega (Madison, Wis.). Protein-binding 96-well plates were from Millipore (Bedford, Mass.). Salts and buffering agents were from Sigma (St. Louis, Mo.). Typically, protein expression was carried out at 26° C. in 50 ml buffered glycerol-complex medium (BMGY) consisting of 1% yeast extract, 2% peptone, 100 mM potassium phosphate buffer, pH 6.0, 1.34% yeast nitrogen base, $4 \times 10^{-5}$% biotin, and 1% glycerol as a growth medium. Induction was performed in 5 ml of buffered methanol-complex medium (BMMY), consisting of 1.5% methanol instead of glycerol in BMGY. Minimal medium is 1.4% yeast nitrogen base, 2% dextrose, 1.5% agar and $4 \times 10^{-5}$% biotin and amino acids supplemented as appropriate.

Generation of Rat EPO Expression Vector.

A truncated form of *Rattus norvegicus* erythropoietin (rEPO), encoding amino acids 27 to 192, was amplified from rat kidney cDNA (BD Biosciences, Palo Alto, Calif.) using Advantage 2 polymerase as recommended by the manufacturer. Briefly, the primers rEPO-for and rEPO-rev (5'-GG-GAATTCGC TCCCCCACGCCTCATTTGCGAC-3' (SEQ ID NO: 1) and 5'-CCTCTAGATCACCTGTCCC CTCTCCT-GCAGGC-3' (SEQ ID NO:2), respectively) were used to amplify a 516 bp product from rat kidney cDNA using the following cycling conditions: 94° C. for 1 min, 1 cycle; 94° C. for 30 seconds, 72° C. for 1 minute, 5 cycles; 94° C. for 30 seconds, 70° C. for 1 minutes, 5 cycles; 94° C. for 20 seconds, 68° C. for 1 minute, 25 cycles. Subsequently the product was cloned into pCR2.1 (Invitrogen, Carlsbad, Calif.), sequenced, and the resultant construct designated pSH603. To generate the yeast expression vector, pSH603 was digested with EcoRI and XbaI to liberate a 506 bp fragment which was subcloned into pPICZαA (Invitrogen, Carlsbad, Calif.), which had previously been digested with the same enzymes. The resultant expression vector was designated pSH692.

Generation of Codon-Optimized Genes in Yeast Expression Cassettes.

Open reading frames for *Homo sapiens* UDP-N-acetylglucosamine-2-epimerase/N-acetylmannosamine kinase (GNE), *H. sapiens* N-acetylneuraminate-9-phosphate synthase (SPS), *H. sapiens* CMP-sialic acid synthase (CSS), *Mus musculus* CMP-sialic acid transporter (CST) and amino acids 40 to 403 of *M. musculus* α-2,6-sialyltransferase (ST) were analyzed by the GENEOPTIMIZER software and codon-optimized for *P. pastoris* expression (GeneArt, Regensburg, Germany). The resultant synthetic DNAs for GNE, SPS, CSS and CST were generated with 5' BsaI and 3' HpaI restriction sites, cloned into a shuttle vector and designated pGLY368, 367, 366 and 369, respectively. The synthetic DNA for ST was generated with 5' AscI and 3' PacI restriction sites, cloned into a shuttle vector and designated pSH660.

To generate the SPS, CSS and CST expression cassettes, the vectors pGLY367, 366 and 369 were digested with BsaI and HpaI to excise 1.1, 1.3, and 1.0 Kb fragments, which were treated with T4 DNA polymerase to remove single strand overhangs (Sambrook, Russell, Molecular Cloning: A Laboratory Manual (Cold Spring Harbor Laboratory Press, Cold Spring Harbor, N. Y., ed. 3rd, 2001)). Subsequently these fragments were subcloned into the vectors pGLY359, 17 and 363 previously digested with NotI and AscI for the former, and NotI and PacI for the latter two, and treated with T4 DNA polymerase. The resultant vectors pSH819, containing SPS in a PpPMA1prom-PpPMA1tt cassette flanked by PacI restriction sites; pSH824, containing CSS in a PpGAPDH-ScCYCtt cassette flanked by 5' BglII and 3' BamHI restriction sites; and pGLY372, containing CST in a PpPMA1prom-PpPMA1tt cassette flanked by RsrII restriction sites.

To generate the ST catalytic domain fused to a yeast localization signal, the *S. cerevisiae* targeting region of Mnt1 was amplified from genomic DNA using Taq DNA polymerase (Promega, Madison, Wis.) and the primers ScMnt1-for and ScMnt1-rev (5'-GGGCGGCCGCCACCATGGC-CCTCTTTCTC AGTAAGAGACT GTTGAG-3' (SEQ ID NO:3) and 5'-CCGGCGCGCCCGATGACTTGTTG TTCAGGGGATATAGATCCTG-3' (SEQ ID NO:4), respectively). The conditions used were: 94° C. for 3 minutes, 1 cycle; 94° C. for 30 seconds, 55° C. for 20 seconds, 68° C. for 1 minute, 30 cycles; 68° C. for 5 minutes, 1 cycle. The resultant 174 bp fragment containing 5' NotI and 3' AscI restriction sites was subcloned in-frame 5' to the codon-optimized ST, creating the vector pSH861. Subsequently this vector was digested with NotI and PacI to excise a 1.3 Kb fragment, containing the ST-fusion, treated with T4 DNA polymerase and subcloned into pGLY361 prepared by digestion with NotI and PacI, and treated with T4 DNA polymerase. The resultant vector, containing the ST-fusion in a PpTEFprom-PpTEFtt cassette flanked by SgfI restriction sites, was designated pSH893.

Generation of Sialic Acid Engineering Vector.

Figure 3A:
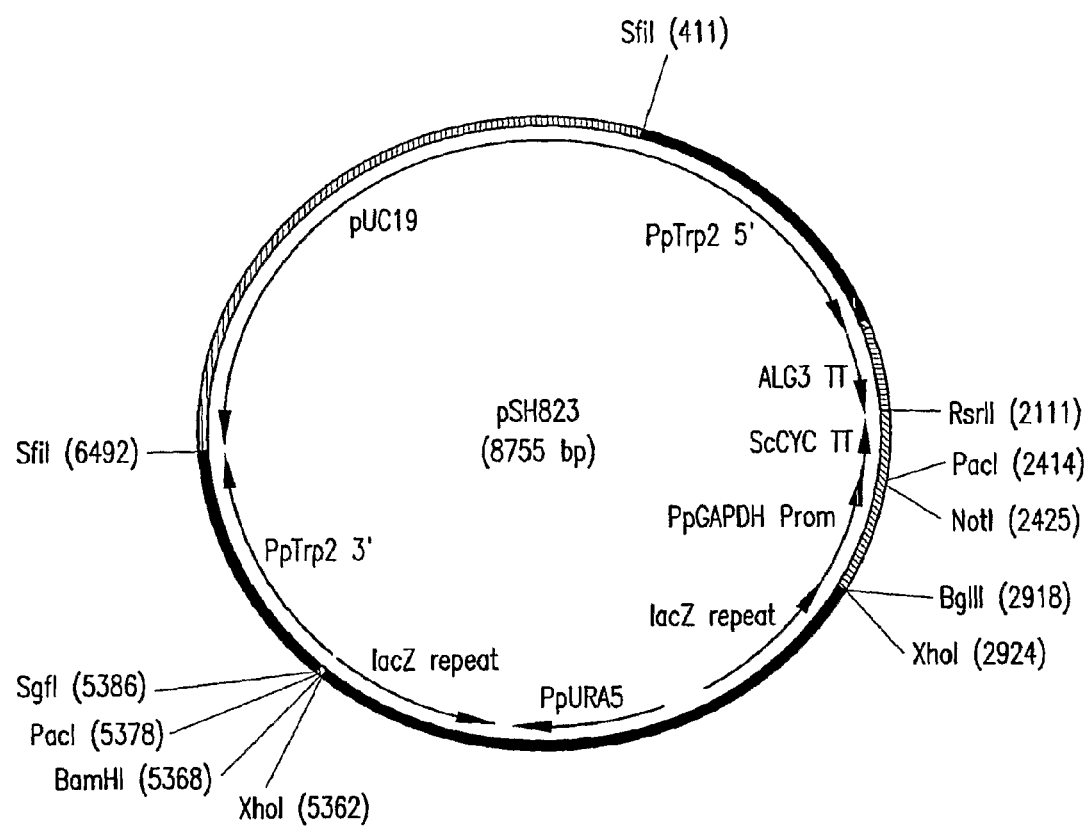
FIG. 3A shows a diagram of knock-in plasmid vector pSH823, which can be used to insert a sequence of interest into the *Pichia pastoris* genome adjacent to the TRP2 ORF. The sequence of interest can be inserted into the plasmid between the PpGAPDH promoter sequence (PpGAPDH) and the ScCYC transcription termination sequence (ScCYC TT). The plasmid further includes the selectable marker PpURA5.

A yeast KINKO expression vector pSH823, containing a *P. pastoris* GAPDH promoter and *S. cerevisiae* CYC transcription terminator, was designed to integrate into the *Pichia* genome downstream of the Trp2 ORF. This vector is illustrated in FIG. 3A. The salient feature of this KINKO vector is that the ALG3 transcription termination sequence is adjacent to the stop codon of the TRP2 ORF. The 2.6 Kb fragment encoding the PMA-CST expression cassette was excised from pGLY372 using the restriction enzyme RsrII and subcloned into pSH823 digested with the same enzyme. The resultant vector in which the PMA-CST and GAPDH expression cassettes were aligned in the same direction was designated pSH826. Subsequently this vector was digested with the restriction enzymes NotI and PacI and the single strand overhangs removed with T4 DNA polymerase (Sambrook, Russell, Molecular Cloning: A Laboratory Manual (Cold Spring Harbor Laboratory Press, Cold Spring Harbor, N. Y., ed. 3rd, 2001)).

Into this linearized KINKO construct, the 2.2 Kb fragment of GNE, isolated from pGLY368 by digestion with BsaI and HpaI, and treated with T4 DNA polymerase to remove single strand overhangs, was subcloned. This vector was designated pSH828. Subsequently this vector was digested with PacI, into which the 2.7 Kb PacI fragment of pSH819, encoding the PMA-SPS expression cassette, was subcloned. The vector produced, in which the PMA-SPS expression cassette was aligned in the opposite orientation to the GAPDH expression cassette, was designated pSH830. At this stage the URA5 marker was replaced with HIS1 by excising the 2.4 Kb URA5 fragment from pSH830 using XhoI and replacing it with the 1.8 Kb fragment of HIS1 from pSH842 digested with the same enzyme. The resultant vector in which the HIS1 ORF was aligned in the same direction as GAPDH-GNE expression cassette was designated pSH870. Subsequently, this vector was digested with BamHI and the 2.1 Kb fragment from pSH824 isolated by digestion with BamHI and BglII, containing the GAPDH-CSS expression cassette, was subcloned.

Figure 3B:
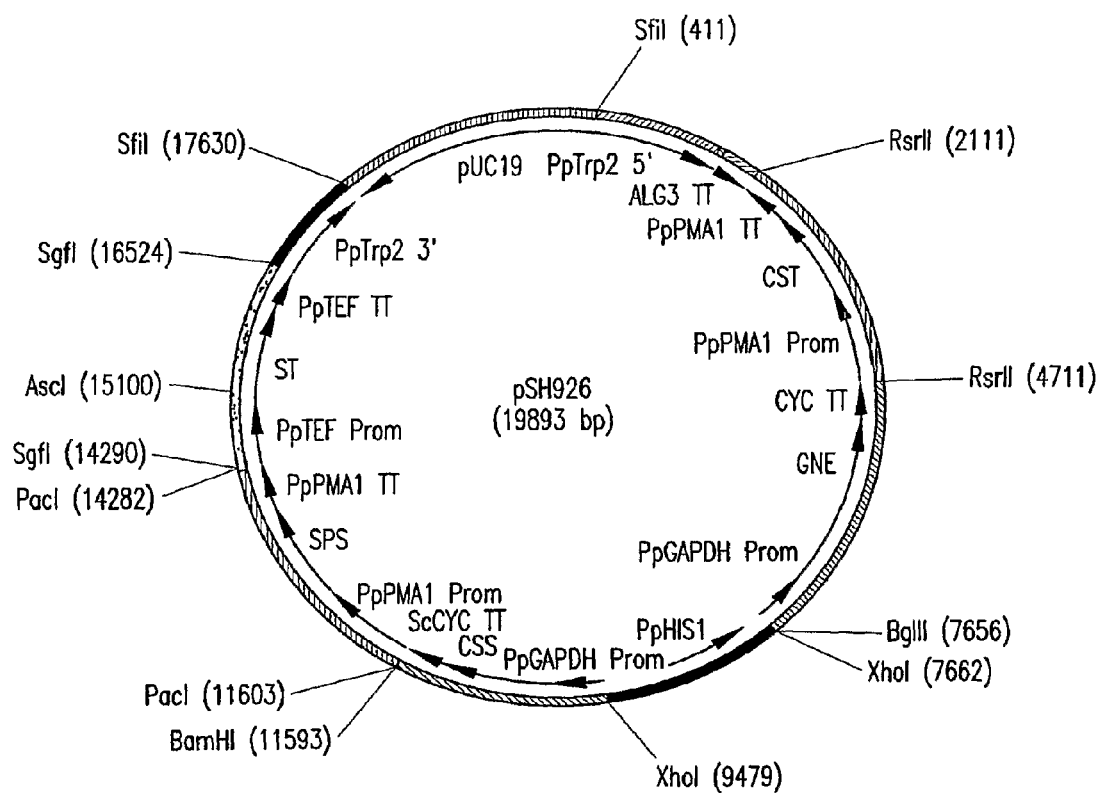
FIG. 3B shows a diagram of knock-in plasmid vector pSH926, which was used to insert five ORFs into the *Pichia pastoris* genome adjacent to the TRP2 ORF. The ORFs encode *Homo sapiens* UDP-N-acetylglucosamine-2-epimerase/N-acetylmannosamine kinase (GNE), *H. sapiens* N-acetylneuraminate-9-phosphate synthase (SPS), *H. sapiens* CMP-sialic acid synthase (CSS), *Mus musculus* CMP-sialic acid transporter (CST) and a fusion protein consisting of amino acids 40 to 403 of *M. musculus* α-2,6-sialyltransferase (ST) and the *S. cerevisiae* targeting region of Mnt1. Each ORF has its own promoter and termination sequence. The plasmid further includes the selectable marker PpHIS1.

The KINKO vector generated, in which the newly introduced expression cassette was orientated in the opposite direction as the GAPDH-GNE cassette, was designated pSH872. Next, the 2.2 Kb expression cassette containing the TEF-ST was digested with SgfI from pSH893 and subcloned into pSH872 digested with the same enzyme. The vector generated, in which the TEF-ST cassette was orientated in the opposite direction as the GAPDH-GNE cassette, was designated pSH926. This KINKO vector, which is used to insert expression cassettes for the CST, GNE CSS, SPS, and ST genes and HIS1 marker into the intergenic region created after the TRP2 ORF, is shown in FIG. 3B.

Generation of Yeast Strains

The *P. pastoris* strain NRRL-Y11430 was transformed with vector pSH692 (encodes rEPO) by electroporation and selected on YPD-Zeocin plates at 26° C. Several clones were screened for expression of rEPO by growth in BMGY and expression in BMMY media, as described above. A clone demonstrating expression was designated YSH551.

A *P. pastoris* glyco-engineered cell line RDP750 [Δoch1, Δpno1, Δmnn4B, Δbmt2, Δhis1, *Kluyveromyces lactis* and *M. musculus* UDP-GlcNAc transporters, *M. musculus* L-1,2-MnsI, *H. sapiens* β-1,2-GlcNAc transferase I, *Rattus norvegicus* β-1,2-GlcNAc transferase II, *Drosophila melanogaster* MnsII, *Schizosaccharomyces pombe* Gal epimerase, *D. melanogaster* UDP-Gal transporter, *H. sapiens* β-1,4-galactosyltransferase] expressing GS5.0 glycans (Li et al., Nat Biotechnol 24, 210 (2006)), was transformed with pSH692. A resultant clone, expressing rEPO, was designated RDP762.

To improve the protein expression levels obtained from this strain, the histidine auxotrophy was complemented by transformation with pJN702 (3), and selected on histidine drop-out minimal plates. The resultant strain was designated YSH557.

To generate a strain with GS6.0 glycans, strain RDP762 above was then transformed with pSH926 and selected on histidine drop-out minimal plates for complementation of the histidine auxotrophy. The resultant strain was designated YSH597.

Protein and Glycan Analysis.

Recombinant rEPO was expressed, described above, and Ni-chelate column purified (Choi et al., Proc Natl Acad Sci USA 100, 5022 (2003); Hamilton et al., Science 301, 1244 (2003)). The resultant protein was analyzed by SDS-PAGE (Laemmli, Nature 227, 680 (1970)) and stained for visualization with coomassie blue. For glycan analysis, the glycans were released from rEPO by treatment with PNGase-F (Choi et al., Proc Natl Acad Sci USA 100, 5022 (2003); Hamilton et al., Science 301, 1244 (2003)). Released glycans were analyzed by MALDI/Time-of-flight (TOF) mass spectrometry to confirm glycan structures (Choi et al., Proc Natl Acad Sci USA 100, 5022 (2003)). To quantitate the relative amount of neutral and charged glycans present, the N-glycosidase F released glycans were labeled with 2-aminobenzidine (2-AB) and analyzed by HPLC.

The conditions used have been previously described (Choi et al., Proc Natl Acad Sci USA 100, 5022 (2003)), with the exception that the elution profile has been modified to: a bi-phasic linear solvent gradient (80% A: 20% B to 40% A: 60% B) over 30 minutes, and (40% A: 60% B to 0% A: 100% B) over 30 minutes, to elute neutral glycans and charged glycans respectively. The column was subsequently eluted isocratically at 100% B for 5 minutes, a linear solvent gradient (0% A: 100% B to 80% A: 20% B) over 5 minutes and isocratically (80% A: 20% B) for 10 minutes in preparation for the next sample. Solvent A was acetonitrile, and solvent B was an aqueous solution of ammonium formate, 50 mM (pH 4.5). The percentage of neutral, GS5.5 and GS6.0 glycans was calculated using peak area of each species (eluting at 20 to 35 minutes, 38 to 45 minutes, and 62 to 68 minutes, respectively) relative to the total peak area.

Preparation of rEPO for In Vivo Characterization.

Strains YSH551 and YSH597 were grown in 2.41 BMGY in baffled shake flasks and induced in 240 ml BMMY to obtain sufficient rEPO with wild-type and GS6.0 glycans, respectively. Recombinant rEPO was captured from the supernatant of the wt and GS6.0 strains using metal affinity chromatography using Streamline Chelating packed on a K9/15 column (0.9×13 cm; GE Bioscience, Piscataway, N.J.) and charged with five column volumes of 50 mM nickel sulfate. The charged column was equilibrated with five column volumes of Buffer A (20 mM Tris, pH8, 200 mM NaCl). 150 ml of culture supernatant, adjusted to pH 8, was loaded onto the column at a flow rate of 3 ml/minutes. The column was washed with buffer A until the A280 reached baseline and rEPO eluted using a linear gradient of 10 column volumes between buffer A and buffer B (20 mM Tris, pH8, 200 mM NaCl, 150 mM imidazole). Fractions from the gradient elution were run on 4-20% SDS-PAGE and rEPO containing fractions were pooled and buffer exchanged to 20 mM MES pH6.0, using an Amicon Ultra centrifugal filter device (MWCO 5,000).

The pooled rEPO fraction from metal chelating chromatography step was further purified by cation exchange chromatography using SP Sepharose Fast Flow (GE Biosciences, Piscataway, N.J.) packed in a K9/15 column (0.9×13 cm). The SP Sepharose FF column was equilibrated with 5 column volumes of buffer C (20 mM MES, pH 6). The sample in buffer C was loaded on to the column at a flow rate of 3 ml/minutes. The column was subsequently washed with 5 column volumes each with buffer C, buffer D (20 mM MES, pH 6, 5 mM CHAPS, 5 mM EDTA) and again with buffer C. Recombinant rEPO was eluted from the column with a linear gradient (10 column volumes) between buffer C and buffer E (20 mM MES, pH 6, 1 M NaCl). Recombinant rEPO containing fractions were identified by SDS-PAGE, pooled and buffer exchanged using an Amicon centrifugal filter device (MWCO 5,000), to phosphate buffered saline pH 7.3 and stored at 4° C.

In Vivo Potency Studies.

Healthy 9 week old BalbC mice (Charles River, Wilmington, Mass.) were injected thrice weekly (n=5/treatment group). Base-line hematocrit values were determined one day prior to the first injection. Mice were bled on days 8 and 15 after first injection for determining hematocrit. Blood was obtained by using a heparinized capillary tube inserted into the orbital sinus. Hematocrit values were determined by using a standard procedure of spinning the micro-capillary tubes at 12,000 rpm for 5 minutes in micro-hematocrit centrifuge.

Results

Figure 4:
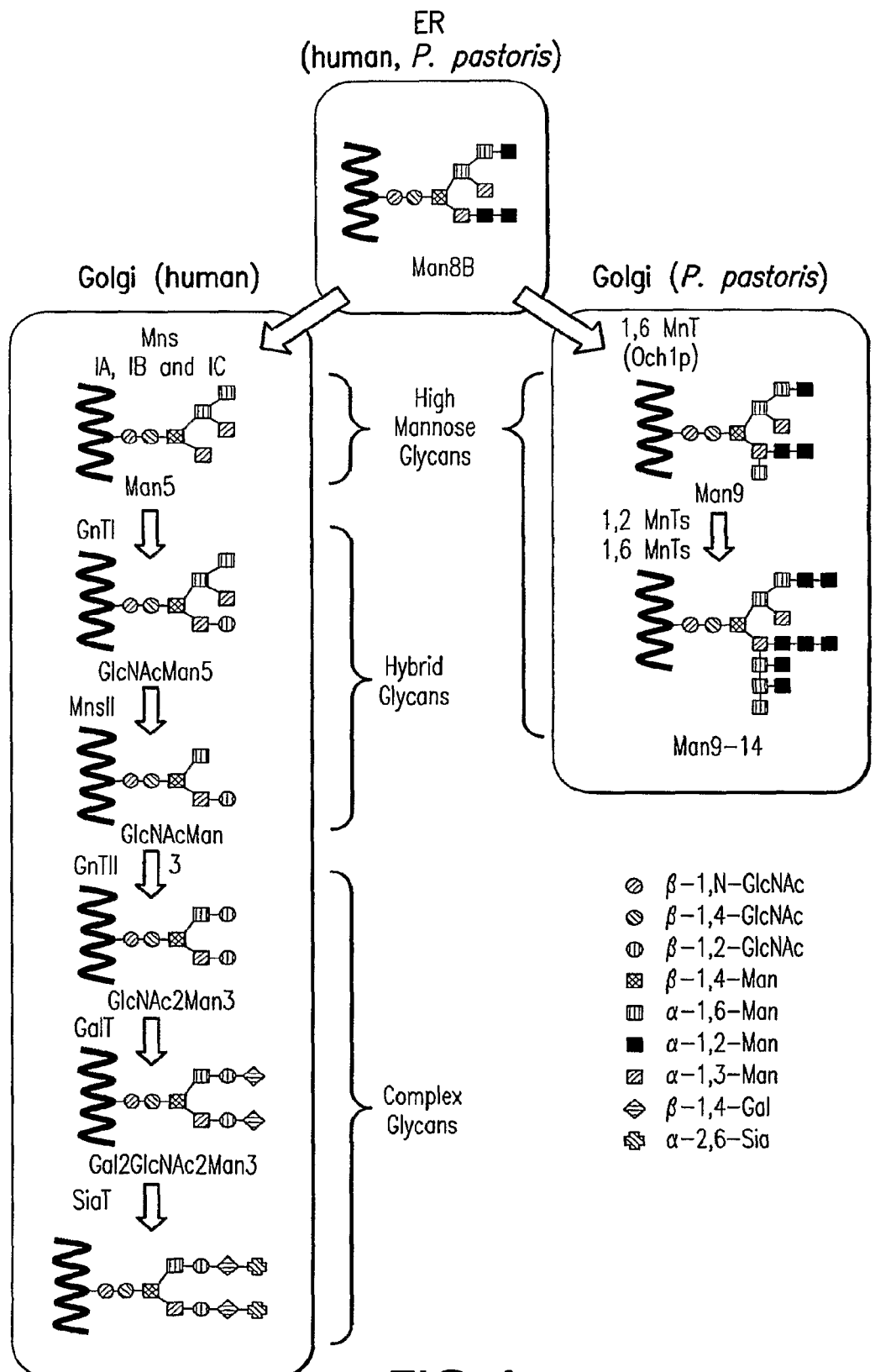
FIG. 4 shows a comparison of the N-linked glycosylation pathways in humans and in *P. pastoris*. Mns; α 1,2-mannosidase, MnsII; mannosidase II, GnT1; β 1,2-N-acetylglucosaminyltransferase I, GnTII; β1,2-N-acetylglucosaminyltransferase I, GalT; β 1,4-galactosyltransferase, SiaT; α 2,6-sialyltransferase, MnT; mannosyltransferase.
Figure 5:
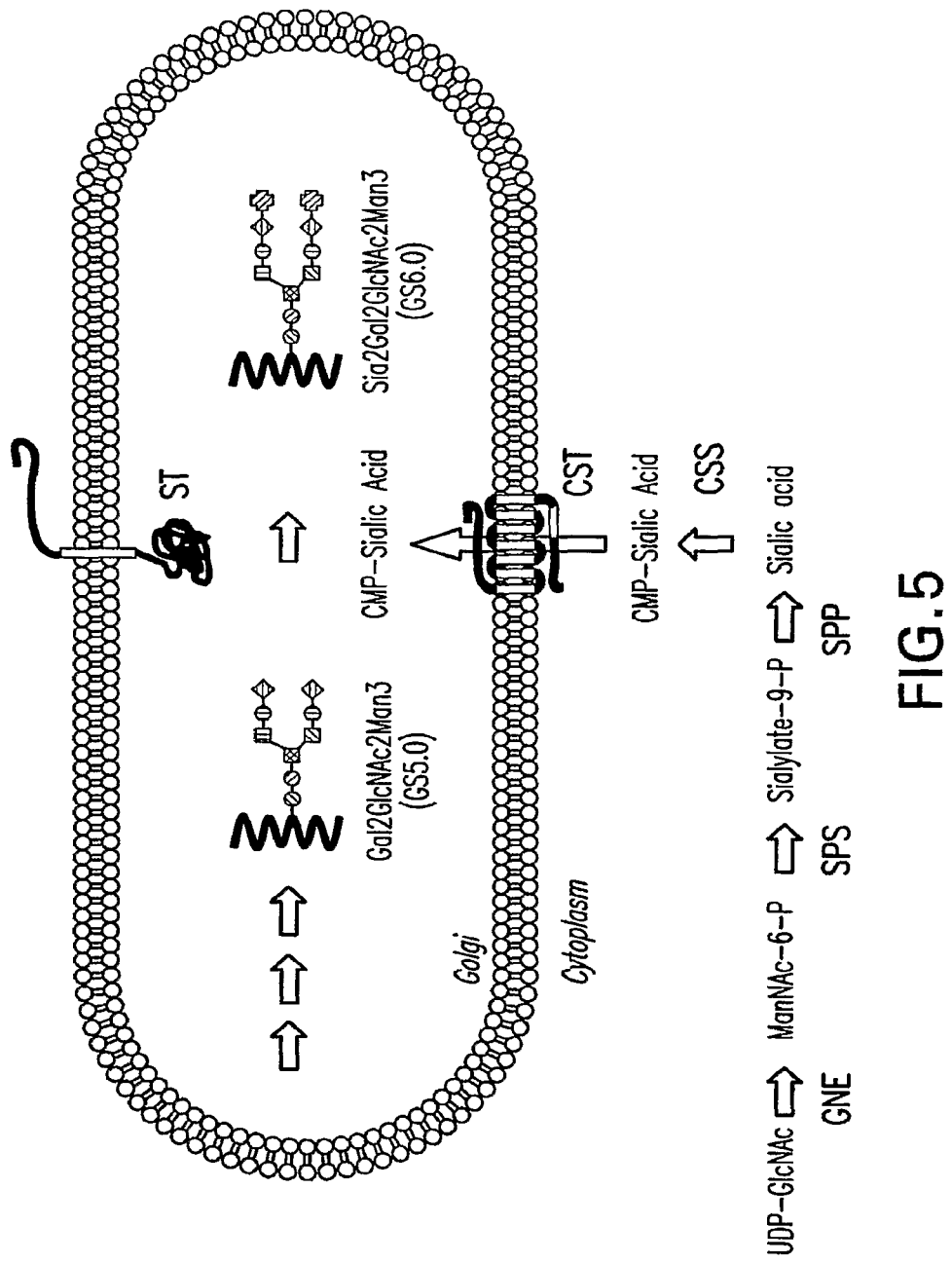
FIG. 5 shows the glyco-engineering steps required for sialic acid transfer in the yeast Golgi. Endogenous UDP-GlcNAc, present in the yeast cytoplasm, is converted to CMP-sialic acid and translocated into the Golgi lumen, by the CMP-sialic acid transporter (CST). Subsequently sialic acid from CMP-sialic acid is transferred onto the acceptor glycan by the sialyltransferase (ST). Components of the biosynthetic pathway: UDP-N-acetylglucosamine-2-epimerase/N-acetylmannosamine kinase (GNE), N-acetylneuraminate-9-phosphate synthase (SPS), sialylate-9-P phosphatase (SPP) and CMP-sialic acid synthase (CSS). Glycan structures are described in FIG. 4.

Here we demonstrate that the core repertoire of human glycosylation reactions (FIG. 4), which involve the sequential removal of mannose by two distinct mannosidases (i.e., α-1,2-mannosidase and mannosidase II), the addition of N-acetylglucosamine (by N-acetylglucosaminyltransferase I and II), the addition of galactose (by β-1,4-galactosyltransferase), and finally the addition of sialic acid by sialyltransferase can be functionally replicated in yeast. Sialylation, the final step of human glycosylation, is particularly difficult to accomplish in yeast, since wild-type yeast lacks all four prerequisites: (i) the ability to produce the N-glycosylated precursors terminating in β-1,4-galactose, (ii) the biosynthetic capability to produce the sugar nucleotide precursor CMP-sialic acid (specifically CMP-N-acetylneuraminic acid, CMP-NANA), (iii) the transporter to shuttle CMP-sialic acid into the Golgi, and (iv) a sialyltransferase to transfer sialic acid to terminal galactose on the nascent glycoprotein (FIG. 5). All of these elements must work at high efficiency to allow for the production of sialylated glycoproteins in a glyco-engineered yeast strain. Moreover, organelle specific targeting of several elements is required to permit these functions to occur in concert.

Figure 6A:
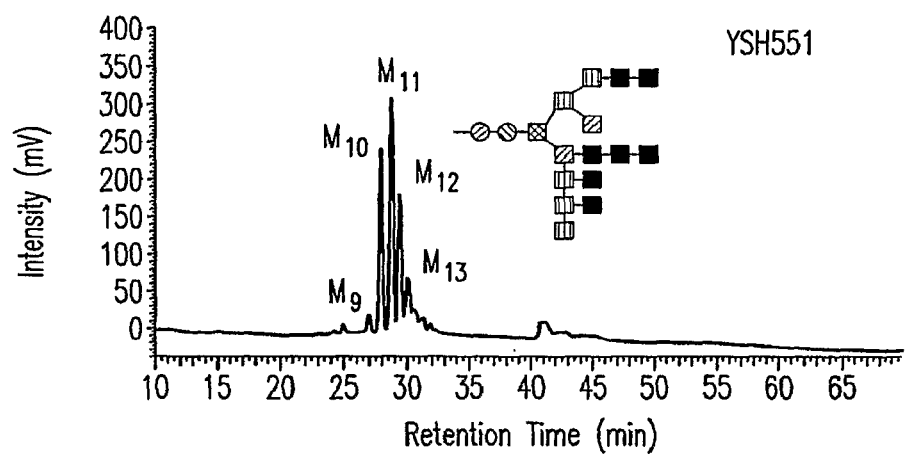
FIG. 6A shows an HPLC characterization of N-linked glycans released from recombinant rEPO secreted from *P. pastoris* strain YSH551 and purified from culture supernatants by Ni-affinity chromatography. Glycans were released from rEPO by PNGase-F treatment and labeled with 2-AB prior to HPLC analysis. Glycan structures are described in FIG. 1.
Figure 6B:
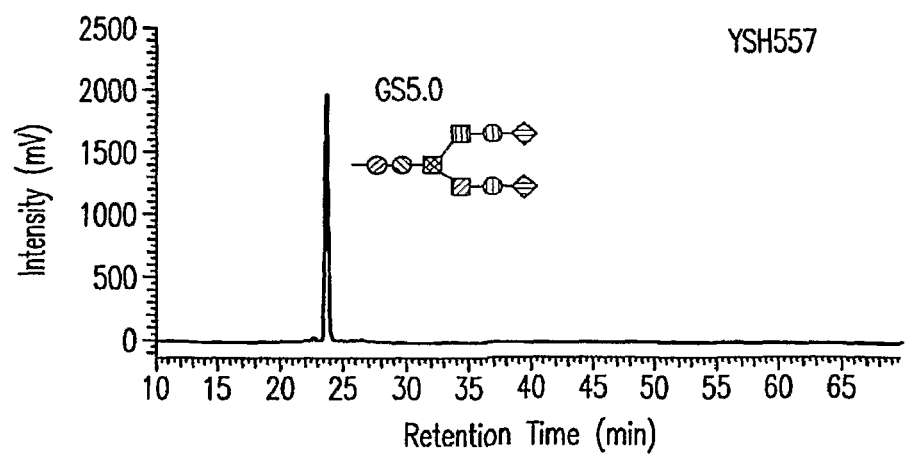
FIG. 6B shows an HPLC characterization of N-linked glycans released from recombinant rEPO secreted from *P. pastoris* strain YSH557. Glycans were released from rEPO by PNGase-F treatment and labeled with 2-AB prior to HPLC analysis. Elution times for commercial glycan standards corresponding to GS5.0 was 24 minutes. Glycan structures are described in FIG. 1.

In previous work, we reported a glyco-engineered strain of $P.$ pastoris that produces terminally galactosylated bi-antennary glycans of the complex type $Gal_2GlcNAc_2Man_3GlcNAc_2$ (i.e., Glycan Structure 5.0, GS5.0) (Li et al., Nat Biotechnol 24, 210 (2006)). This strain RDP750 [Δoch1, Δpno1, Δmnn4B, Δbmt2, Δhis1, Kluyveromyces lactis and Mus musculus UDP-GlcNAc transporters, Mus musculus α-1,2-MnsI, Homo sapiens β-1,2-GlcNAc transferase I, Rattus norvegicus 1-1,2-GlcNAc transferase II, Drosophila melanogaster MnsII, Schizosaccharomyces pombe Gal epimerase, D. metanogaster UDP-Gal transporter, H. sapiens β-1,4-galactosyltransferase] was transformed with an expression plasmid encoding for rEPO, to generate strain YSH557 (Hamilton et al., Science 313:1441-1443 (2006)). Secreted rEPO from this strain consisted predominantly of GS5.0 N-glycans (FIG. 6B). For comparison, the same construct was used to transform wild-type $P.$ pastoris NRRL-Y11430, resulting in strain YSH551, which secreted rEPO with mostly high-mannose N-glycans that are typical for this yeast (Hamilton et al., Science 301, 1244 (2003)) (FIG. 6A). Both strains express rEPO at about the same level (about 20 mg/l), even though the secreted protein differs significantly with respect to N-glycosylation (FIGS. 6A and 6B).

To further humanize the glycosylation machinery we set out to engineer the GS5.0 producing strain to perform the final step of human glycosylation, the addition of terminal sialic acid. To accomplish this we transformed $P.$ pastoris strain RDP762 with a range of DNA constructs encoding for enzymes involved in CMP-sialic acid biosynthesis, CMP-sialic acid transport and sialic acid transfer to the nascent glycoprotein. In total, five enzymes were selected: $H.$ sapiens UDP-N-acetylglucosamine-2-epimerase/N-acetylmannosamine kinase (GNE), $H.$ sapiens N-acetylneuraminate-9-phosphate synthase (SPS), $H.$ sapiens CMP-sialic acid synthase sialyltransferases linked to yeast type-II transmembrane localization peptides (ST).

Over 120 permutations of alternative CMP-sialic acid pathways, CSTs and STs were screened. From this screen, we identified a small number of combinations displaying significant sialyltransferase activity and producing predominantly complex glycan structures. However, taking this approach, we were unable to obtain glycan compositions containing greater than 60% GS6.0 ($Sia_2Gal_2GlcNAc_2Man_3GlcNAc_2$), indicating a limitation in the sialic acid transfer machinery (data not shown).

Figure 6C:
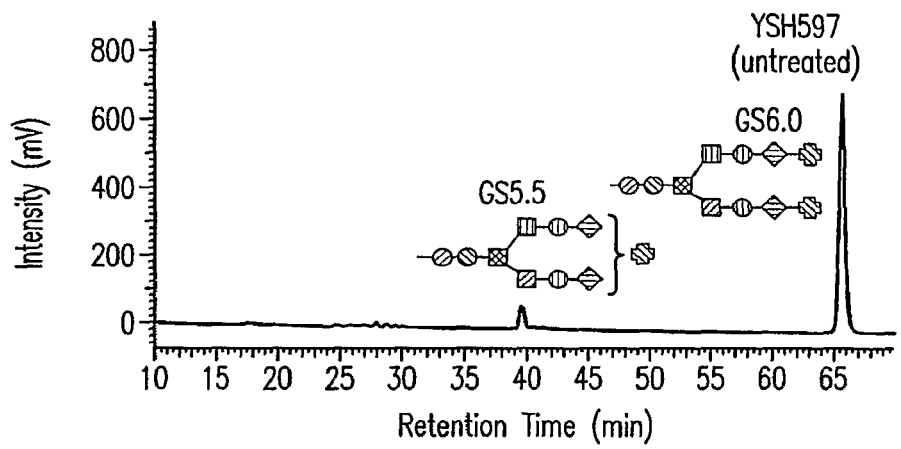
FIG. 6C shows an HPLC characterization of N-linked glycans released from recombinant rEPO secreted from *P. pastoris* strain YSH597. Glycans were released from rEPO by PNGase-F treatment and labeled with 2-AB prior to HPLC analysis. Elution times for commercial glycan standards corresponding to GS5.5 and 6.0 were 40 and 66 minutes, respectively. Glycan structures are described in FIG. 1.
Figure 6D:
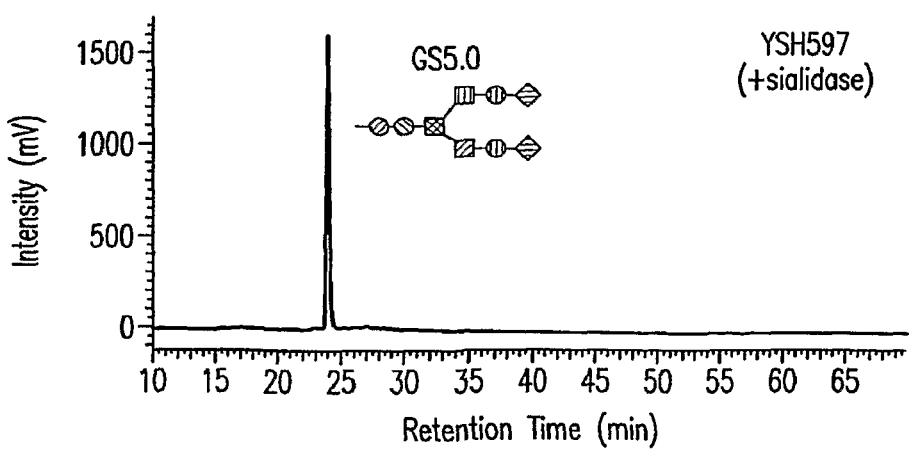
FIG. 6D shows an HPLC that confirms that glycans secreted from YSH597 in FIG. 6C contained sialic acid. The sample was treated with α-2,3-/-2,6-/-2,8-sialidase. Elution time for commercial glycan standards corresponding to GS5.0 was 24 minutes. Glycan structures are described in FIG. 1.

To overcome this limitation, we codon-optimized GNE, SPS, CSS, CST and screened additional ST/leader fusions. As such, we identified the catalytic domain of mouse α-2,6-ST, fused to the $S.$ cerevisiae mannosyltransferase 1 (Mnt1) targeting signal as particularly effective. In order to consolidate these efforts we cloned all five genes into a single expression vector, pSH926 (Hamilton et al., Science 313:1441-1443 (2006)). Transformation of this vector into RDP762 complemented the histidine auxotrophy of the host, while targeting the gene cluster to the Trp2 locus of the Pichia genome. The resulting strain, designated YSH597, was cultured in shake flasks and induced to secrete rEPO. Analysis of the N-glycans isolated from rEPO displayed a glycan composition that consisted predominantly of sialylated glycan structures GS6.0 (90.5%) and GS5.5 (7.9%, $SiaGal_2GlcNAc_2Man_3GlcNAc_2$) (FIG. 6C). Subsequent treatment of this sample with sialidase showed quantitative conversion to GS5.0 (FIG. 6D), confirming that GS6.0 and GS5.5 were terminally sialylated glycan structures.

Figure 7A:
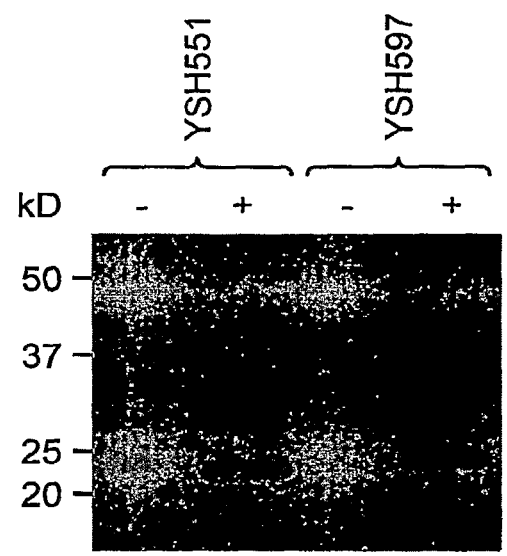
FIG. 7 shows a characterization of recombinant rEPO obtained from *P. pastoris*. SDS-PAGE analysis (A) of recombinant rEPO (2.5 µg, post-purification) secreted from YSH1551 and YSH597 strains, following incubation in the presence (+) or absence (−) of PNGase-F. Comparative hematocrit analysis (B) of recombinant EPO secreted from YSH551 (blue and green bars) and YSH597 (red and yellow bars). Values correspond to days 8 (blue and red bars) and 15 (green and yellow bars), following initial injection. Data presented as mean±S.D. of n=5 mice per dose.
Figure 7B:
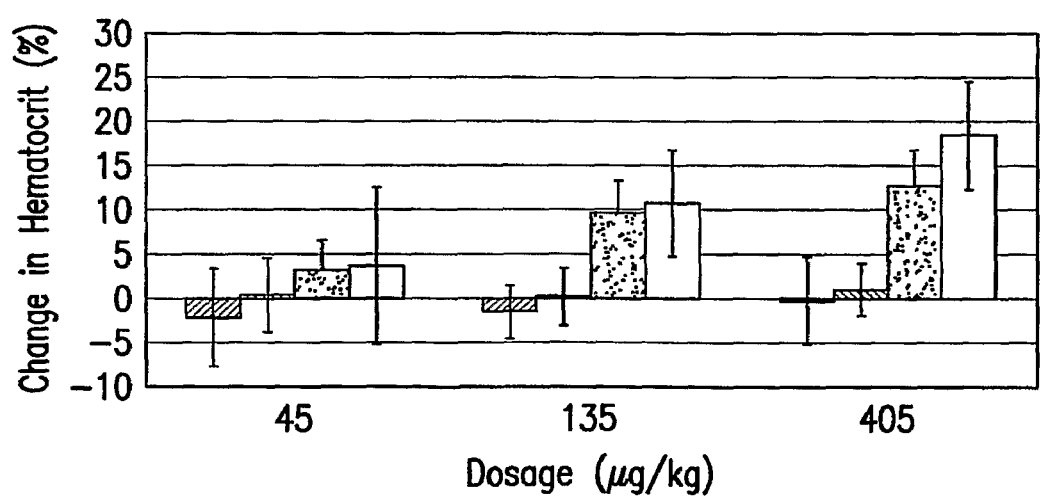

To assess the in vivo activity of different rEPO glycoforms, we purified material from $P.$ pastoris wild-type (YSH551) and the terminally sialylating strain YSH597 (Hamilton et al., Science 313:1441-1443 (2006)). The purified protein was characterized by SDS-PAGE (FIG. 7A); and rEPO from wild-type $P.$ pastoris showed extensive heterogeneity consistent with hyper-glycosylation and the range of high-mannose structure found by HPLC analysis (FIG. 6A). In contrast, rEPO from YSH597 showed a more uniform migration pattern, consistent with the glycan uniformity found by HPLC analysis (FIG. 6C). As expected, when both samples were treated with PNGase-F, to remove the N-glycans, the mass and uniformity of the de-glycosylated material appeared similar (FIG. 7A). To compare the in vivo functionality of these two vastly different glycoforms, animal studies were performed to determine their respective erythropoietic function in vivo. As expected rEPO produced in wild-type yeast had no measurable erythropoietic function whereas rEPO produced in YSH597 showed a dose dependent response consistent with a biologically active form of rEPO FIG. 7B).

In summary, the KINKO vectors enabled construction of yeast cell lines of $P.$ pastoris capable of producing uniform terminally sialylated complex bi-antennary glycoproteins.

BIBLIOGRAPHY

1. Ashwell & Harford, Annu Rev Biochem 51, 531 (1982)
2. Stockert, Physiol Rev 75, 591 (1995)
3. Werten et al., Yeast 15, 1087 (1999)
4. Durand et al., Enzyme and Microbial Technology 10, 341 (1988)
5. Gemmill & Trimble, Biochim Biophys Acta 1426, 227 (1999)
6. Choi et al., Proc Natl Acad Sci USA 100, 5022 (2003)
7. Hamilton et al., Science 301, 1244 (2003)
8. Bobrowicz et al., Glycobiology 14, 757 (2004)
9. Spivak, Blood Rev 3, 130 (1989)
10. Lai et al., J Biol Chem 261, 3116 (1986).
11. Davis et al., Biochemistry 26, 2633 (1987)
12. Fukada et al., Blood 73, 84 (1989)
13. Li et al., Nat Biotechnol 24, 210 (2006)
14. Hamilton et al., Science 313:1441-1443 (2006)
15. Nett et al., Yeast 22, 295 (2005)

```
Sequences
Pichia pastoris PRO1: (SEQ ID NO: 5) Stop codon
1225-1227
GGCCATCGAATTGTCATCGTCTCCTCAGGTGGCATCGCTGTGGGCATGAA

GAGAGTCAACATGAAGCGGAAACCAAAAAAGTTACAGCAAGTGCAGGCAT
```

```
TGGCTGCTATAGGACAAGGCCGTTTGATAGGACTTTGGGACGACCTTTTC

CGTCAGTTGAATCAGCCTATTGCGCAGATTTTACTGACTAGAAGGGATTT

GGTCGATTACACCCAGTTTGAACGCTGAAAATACATTGGAACAGCTTATT

AAAATGGGTATTATTCCTATTGTCAATGAGAATGACACCCTATCCATTCA

AGAAATCAAATTTGGTGACAATGACACCTTATCCGCCATAACAGCTGGTA

TGTGTCATGCAGACTACCTGTTTTTGGTGACTGATGTGGACTGTCTTTAC

ACGGATAACCCTCGTACGAATCCGGACGCTGAGCCAATCGTGTTAGTTAG

AAATATGAGGAATCTAAACGTCAATACCGAAAGTGGAGGTTCCGCCGTAG

GAACAGGAGGAATGACAACTAAATTGATCGCAGCTGATTTGGGTGTATCT

GCAGGTGTTACAACGATTATTTGCAAAAGTGAACATCCCGAGCAGATTTT

GGACATTGTAGAGTACAGTATCCGTGCTGATAGAGTCGAAAATGAGGCTA

AATATCTGGTCATCAACGAAGAGGAAACTGTGGAACAATTTCAAGAGATC

AATCGGTCAGAACTGAGGGAGTTGAACAAGCTGGACATTCCTTTGCATAC

ACGTTTCGTTGGCCACAGTTTTAATGCTGTTAATAACAAAGAGTTTTGGT

TACTCCATGGACTAAAGGCCAACGGAGCCATTATCATTGATCCAGGTTGT

TATAAGGCTATCACTAGAAAAAACAAAGCTGGTATTCTTCCAGCTGGAAT

TATTTCCGTAGAGGGTAATTTCCATGAATACGAGTGTGTTGATGTTAAGG

TAGGACTAAGAGATCCAGATGACCCACATTCACTAGACGCCAATGAAGAA

CTTTACGTCGTTGGCCGTGCCCGTTGTAATTACCCCAGCAATCAAATCAA

CAAAATTAAGGGTCTACAAAGCTCGCAGATCGAGCAGGTTCTAGGTTACG

CTGACGGTGAGTATGTTGTTCACAGGGACAACTTGGCTTTCCCAGTATTT

GCCGATCCAGAACTGTTGGATGTTGTTGAGAGTACCCTGTCTGAACAGGA

GAGAGAATCCAAACCAAATAAATAGAATTTCACATATGCTGCTTGATTAT

GTAATTATACCTTGCGTTCGATGGCATCGATTTCCTCTTCTGTCAATCGC

GCATCGCATTAAAAGTATACTTTTTTTTTTTCCTATAGTACTATTCGCC

TTATTATAAACTTTGCTAGTATGAGTTCTACCCCCAAGAAAGAGCCTGAT

TTGACTCCTAAGAAGAGTCAGCCTCCAAAGAATAGTCTCGGTGGGGGTAA

AGGCTTTAGTGAGGAGGGTTTCTCCCAAGGGACTTCAGCGCTAAGCATA

TACTAAATCGTCGCCCTAACACCGAAGGCTCTTCTGTGGCTTCGAACGTC

ATCAGTTCGTCATCATTGCAAAGGTTACCATCCTCTGGATCTGGAAGCGT

TGCTGTGGGAAGTGTGTTGGGATCTTCGCCATTAACTCTTTCTGGAGGGT

TCCACGGGCTTGATCCAACCAAGAATAAAATAGACGTTCCAAAGTCGAAA

CAGTCAAGGAGACAAAGTGTTCTTTCTGAGATGATTTCCACTTCTCATGC

AGCTAGAAATGATCACTCAGAGCAGCAGTTACAAACTGGACAACAATCAG

AACAAAAGAAGAAGATGGTAGTCGATCTTCTTTTTCTGTTTCTTCCCCC

GCAAGAGATATCCGGCACCCAGATGTACTGAAAACTGTCGAGAAACATCT

TGCCAATGACAGCGAGATCGACTCATCTTTACAACTTCAAGGTGGAGATG

TCACTAGAGGCATTTATCAATGGGTAACTGGAGAAAGTAGTCAAAAGATA

ACCCGCCTTTGAAACGAGCAAATAGTTTTAATGATTTTCTTCTGTGCAT

GGTGACGAGGTAGGCAAGGCAGATGCTGACCACGATCGTGAAAGCGTATT

CGACGAGGATGATATCTCCATTGATGATATCAAAGTTCCGGGAGGGATGC
```

```
GTCGAAGTTTTTTATTACAAAAGCATAGAGACCAACAACTTTCTGGACTG

AATAAAACGGCTCACCAACCAAAACAACTTACTAAACCTAATTTCTTCAC

GAACAACTTTATAGAGTTTTTGGCATTGTATGGGCATTTTGCAGGTGAAG

ATTTGGAGGAAGACGAAGATGAAGATTTAGACAGTGGTTCCGAATCAGTC

GCAGTCAGTGATAGTGAGGGAGAATTCAGTGAGGCTGACAACAATTTGTT

GTATGATGAAGAGTCTGTCCTATTAGCACCTAGTACCTCCAACTATGCGA

GATCAAGAATAGGAAGTATTCGTACTCCTACTTATGGATCTTTCAGTTCA

AATGTTGGTTCTTCGTCTATTCATCAGCAGTTAATGAAAAGTCAAATCCC

GAAGCTGAAGAAACGTGGACAGCACAAGCATAAAACACAATCAAAAATAC

GCTCGAAGAAGCAAACTACCACCGTAAAAGCAGTGTTGCTGCTATTAAA
```

*Pichia pastoris* TRP2: (SEQ ID NO: 6) Stop codon 1300-1302

```
ACTGGGCCTTTAGAGGGTGCTGAAGTTGACCCCTTGGTGCTTCTGGAAAA

AGAACTGAAGGGCACCAGACAAGCGCAACTTCCTGGTATTCCTCGTCTAA

GTGGTGGTGCCATAGGATACATCTCGTACGATTGTATTAAGTACTTTGAA

CCAAAAACTGAAAGAAAACTGAAAGATGTTTTGCAACTTCCGGAAGCAGC

TTTGATGTTGTTCGACACGATCGTGGCTTTTGACAATGTTTATCAAAGAT

TCCAGGTAATTGGAAACGTTTCTCTATCCGTTGATGACTCGGACGAAGCT

ATTCTTGAGAAATATTATAAGACAAGAGAAGAAGTGGAAAAGATCAGTAA

AGTGGTATTTGACAATAAAACTGTTCCCTACTATGAACAGAAAGATATTA

TTCAAGGCCAAACGTTCACCTCTAATATTGGTCAGGAAGGGTATGAAAAC

CATGTTCGCAAGCTGAAAGAACATATTCTGAAAGGAGACATCTTCCAAGC

TGTTCCCTCTCAAAGGGTAGCCAGGCCGACCTCATTGCACCCTTTCAACA

TCTATCGTCATTTGAGAACTGTCAATCCTTCTCCATACATGTTCTATATT

GACTATCTAGACTTCCAAGTTGTTGGTGCTTCACCTGAATTACTAGTTAA

ATCCGACAACAACAACAAAATCATCACACATCCTATTGCTGGAACTCTTC

CCAGAGGTAAAACTATCGAAGAGGACGACAATTATGCTAAGCAATTGAAG

TCGTCTTTGAAAGACAGGGCCGAGCACGTCATGCTGGTAGATTTGGCCAG

AAATGATATTAACCGTGTGTGTGAGCCCACCAGTACCACGGTTGATCGTT

TATTGACTGTGGAGAGATTTTCTCATGTGATGCATCTTGTGTCAGAAGTC

AGTGGAACATTGAGACCAAACAAGACTCGCTTCGATGCTTTCAGATCCAT

TTTCCCAGCAGGTACCGTCTCCGGTGCTCCGAAGGTAAGAGCAATGCAAC

TCATAGGAGAATTGGAAGGAGAAAGAGAGGTGTTTATGCGGGGGCCGTA

GGACACTGGTCGTACGATGGAAAATCGATGGACACATGTATTGCCTTAAG

AACAATGGTCGTCAAGGACGGTGTCGCTTACCTTCAAGCCGGAGGTGGAA

TTGTCTACGATTCTGACCCCTATGACGAGTACATCGAAACCATGAACAAA

ATGAGATCCAACAATAACACCATCTTGGAGGCTGAGAAAATCTGGACCGA

TAGGTTGGCCAGAGACGAGAATCAAAGTGAATCCGAAGAAAACGATCAAT

GAACGGAGGACGTAAGTAGGAATTTATGTAATCATGCCAATACATCTTTA

GATTTCTTCCTCTTCTTTTTAACGAAAGACCTCCAGTTTTGCACTCTCGA

CTCTCTAGTATCTTCCCATTTCTGTTGCTGCAACCTCTTGCCTTCTGTTT
```

-continued
```
CCTTCAATTGTTCTTCTTTCTTCTGTTGCACTTGGCCTTCTTCCTCCATC
TTTCGTTTTTTTTCAAGCCTTTTCAGCAGTTCTTCTTCCAAGAGCAGTTC
TTTGATTTTCTCTCTCCAATCCACCAAAAAACTGGATGAATTCAACCGGG
CATCATCAATGTTCCACTTTCTTTCTCTTATCAATAATCTACGTGCTTCG
GCATACGAGGAATCCAGTTGCTCCCTAATCGAGTCATCCACAAGGTTAGC
ATGGGCCTTTTTCAGGGTGTCAAAAGCATCTGGAGCTCGTTTATTCGGAG
TCTTGTCTGGATGGATCAGCAAAGACTTTTTGCGGAAAGTCTTTCTTATA
TCTTCCGGAGAACAACCTGGTTTCAAATCCAAGATGGCATAGCTGTCCAA
TTTGAAAGTGGAAAGAATCCTGCCAATTTCCTTCTCTCGTGTCAGCTCGT
TCTCCTCCTTTTGCAACAGGTCCACTTCATCTGGCATTTTTCTTTATGTT
AACTTTAATTATTATTAATTATAAAGTTGATTATCGTTATCAAAATAATC
ATATTCGAGAAATAATCCGTCCATGCAATATATAAATAAGAATTCATAAT
AATGTAATGATAACAGTACCTCTGATGACCTTTGATGAACCGCAATTTTC
TTTCCAATGACAAGACATCCCTATAATACAATTATACAGTTTATATATCA
CAAATAATCACCTTTTTATAAGAAAACCGTCCTCTCCGTAACAGAACTTA
TTATCCGCACGTTATGGTTAACACACTACTAATACCGATATAGTGTATGA
AGTCGCTACGAGATAGCCATCCAGGAAACTTACCAATTCATCAGCACTTT
CATGATCCGATTGTTGGCTTTATTCTTTGCGAGACAGATACTTGCCAATG
AAATAACTGATCCCACAGATGAGAATCCGGTGCTCGT
```

*Pichia pastoris* TRP5: (SEQ ID NO: 7) Stop codon 653-365
```
ACGACGGCCAAATTCATGATACACACTCTGTTTCAGCTGGTTTGGACTAC
CCTGGAGTTGGTGCTGAATTGGCTGCCTGGAAAGCAAATGGTAGAGCCCA
ATTTTCCGCTGTAACTGATGCCCAAGCATTAGAGGGATTCAAAATCCTGT
CTGAATTGGAAGGGATCATTCCAGCACTAGAGTCTAGTCATGCAATCTAC
GGCGCATTGCAAATTGCAAAGACTATGTCTTCGGACCAGTCCTTAGTTAT
TAATGTATCTGGAAGGGGTGATAAGGACGTCCAGAGTGTAGCTGAGATTT
TACCTAAATTGGGACCTCAAATTGGATGGGATTTGCGTTTCAGCGAAGAC
ATTACTAAAGAGTGATCGATAGCACAATATTCAACTTGACTGGGTGTTAA
GAACTAAGAGCTCTGGGAAACTTTGTATTTATTACTACCAACACAGTCAA
ATTATTGGATGTGTTTTTTTTCCAGTACATTTCACTGAGCAGTTTGTTA
TACTCGGTCTTTAATCTCCATATACATGCAGATTGTAATACAGATCTGAA
CAGTTTGATTCTGATTGATCTTGCCACCAATATTCTATTTTGTATCAAG
TAACAGAGTCAATGATCATTGGTAACGTAACGGTTTTCGTGTATAGTAGT
TAGAGCCCATCTTGTAACCTCATTTCCTCCCATATTAAAGTATCAGTGAT
TCGCTGGAACGATTAACTAAGAAAAAAAAAATATCTGCACATACTCATCA
GTCTGTAAATCTAAGTCAAAACTGCTGTATGCAATAGAAATCGGATATA
CCTGGATGTTTTTTCCACATAAACAAACGGGAGTTCAGCTTACTTATGGT
GTTGATGCAATTCAGTATGATCCTACCAATAAAACGAAACTTTGGGATTT
TGGCTGTTTGAGGGATCAAAAGCTGCACCTTTACAAGATTGACGGATCGA
CCATTAGACCAAAGCAAATGGCCACCAA
```

*Pichia pastoris* THR1: (SEQ ID NO: 8) Stop codon 1354-1356
```
GAGTCGGCCAGCCCATGACCATGAATGCTTAAAACGCCAACTCCTTCCAT
CTCATTTTCGTACCAGATTATGACTCTTAGGCGGGGAGAATCCCGTCCAG
CATAGCGAACATTTCTTTTTTTTTTTTTTTCGTTTCGCATCTCTCTATC
GCATTCAGAAAAAAATACATATAATTCTTCCAGTTTCCGTCATTCATTAC
GTTTAAAACTACGAAAGTTTTAGCTCTCTTTTGTTTTTGTTTCCTAGATT
CGAAATATTTTCTTTATTGAGTTTAATTTGTGTGGCAGACAATGGTTAGA
TCTTTCACCATCAAAGTGCCTGCTTCCTCAGCAAATATAGGACCGGGGTT
TGACGTTCTGGGATTGGTCTCAACCTTTACTTGGAACTACAAGTCACCAT
TGATCCCAAAATTGATACCTCAAGCGATCCAGAAATGTGTTATTGTCGT
ATGAAGGTGAGGGGGCTGATGAGGTGTCATTGAAAAGTGACGAAAACTTG
ATTACGCGCACAGCTCTCTATGTTCTACGTTGTGACGACGTCAGGACTTT
CCCTAAGGGAACCAAGATTCACGTCATTAACCCTATTCCTCTAGGAAGAG
GCTTGGGATCTTCGGGTGCTGCAGTTGTCGCCGGTGCATTGCTCGGAATT
CCATCGGACAGCTTGGATACTCCAAACAACGTTTACTGGATTACTGTTTG
ATGATAGAACGTCATCCAGATAACATCACCGCAGCTATGGTGGGTGGTTT
CGTTGGATCTTATCTTAGAGATCTTTCACCAGAAGAGACCCAGAGAAAAG
AGATTCCATTAGCAGAAGTCCTGCCAGAACCTCAAGTGGTATTAACACCG
GTCTCAACCCACCAGTGCCTCCAAAAAACATTGGGCACCACATCAAATAC
GGCTGGGCAAAAGAGATCAAATGTATTGCCATTATTCCAGACTTTGAAGT
ATCAACCGCTTCATCTAGAGGCGTTCTTCCAACCACTTACGAGAGACATG
ACATTATTTTCAACCTGCAAAGGATAGCCGTTCTTACCACTGCCCTGACA
CAATCTCCACCAGATCCAAGCTTGATATACCCAGCTATGCAGGACAGGAT
TCACCAACCTTACAGGAAAACTTTGATCCACGGACTGACTGAAATACTGT
CTTCATTCACCCCAGAATTACACAAAGGTTTGTTGGGAATCTGTCTTTCC
GGTGCTGGGCCCACAATATTAGCCCTCGCAACTGAAAAGTTCGATCAGAT
TGCTAAGGACATCATTGCCAGATTTGCTGTCGAAGACATCACCTGTAGTT
GGAAACTCTTGACCCCAGCTCTTGAAGGTTCTGTTGTTGAGGAGCTTGCT
TAATAGAAATTAGAACATCCTCTTTAGATTATGATAATACGTTTTTAACT
TTTCCCCTAACTGTAGTGATGGTATCTGACCCTCTTAGACCTTAGGTTGG
ACCTTCTCGAATTTCCTGCCTCTATCAAAAATCCGACCCTCGACATCGTT
TACGTAGTTTGCAACCAATTAACTAGTACCGGCAGACGTTCAGTGATCAT
GGCTCTCTATACAAATACCCTGATAACGTTTGCATTCCTGACAGTCGGAG
GATGTACGTGCTTATTTTCTTGCTAGTCCCAAATGTTTTGAGATTGCTCC
AATCGTTTTTCAACAATACTAACTGCCAACAAATAGATCTTTTATTCAA
CGGAAATGGGAACAATTCAACGTGGGTGACTTTTTGGAGACTACATCTC
CCTATATGTGGGCAAATCTGGGTATAGCAAGTTGCATTGGATTCTCGGTC
ATTGGTGCTGCATGGGGAATTTTCATAACAGGTTCTTCGATCATCGGTGC
AGGTGTCAAAGCTCCCAGAATCACAACAAAAATTTAATCTCGATCATTT
TCTGTGAGGTGGTGGCTATTTATGGGCTTATTATGGCCATTGT
```

Pichia pastoris LYS1: (SEQ ID NO: 9) Stop codon 1051-1053

AGAGCCGCCCTTACACCTTCGACAGCCAAGGAATTGTTAGATACAGGAAG
ATTTGAAATCTTTGTTGAGGAAAGTAGTCAAAGCACTTTTGCAACCGAAG
AGTATAAAAAGGCGGGCACAAATATTGTACCGGAAGGTTCCTGGGTTGAT
GCCCCAAAAGAGAGAATAATTCTGGGGCTGAAGGAACTCCCAGAGGACAC
TTTTCCCTTAGTACACGAGCATATTCAATTTGCACACTGCTACAAAGACC
AGTCCGGCTGGAAAGATGTGTTAAAAAGATTTCCCGAAGGAAATGGCACT
CTTTATGATCTGGAGTTCTTGGAAAATGATAATGGAAGAAGAGTAGCTGC
TTTTGGCTTCTATGCAGGATTTGCAGGCGCTGCTCTTGGGATTCAAGACT
GGGCGTTCAAACAGACCCATGCGGATCATGAGAATTTACCCGGTGTTTCC
CCCTATGGCAACGAGCAAGCCTTGATCGCCGACGTTAAAAAAGATTTGGA
TGTTGCCGTTTCCAAAACTGGAAGAAAACCAAAGATCTTGGTTATTGGTG
CCCTTGGTCGTTGTGGATCTGGTGCTATTGACTTACTTAAGAAAGTGGGT
ATTCCCGATGAGAACATCTCTAAGTGGGACGTTAACGAACCAGTATCGGA
GGCCCTTTCAAACAAATTGCAGAGTCCGACATATTCATTAATTGTATATA
CCTCTCACAGCCAATTCCTCCTTTTATCGACTTGAATACTCTAAACTTCG
AGGACAGAGCTCTAAGAACAATTGTGGATGTTTCTGCGGACACCACCAAC
CCACACAATCCAATCCCTGTTTATACTGTTGCGACAGTATTTTCAGATCC
AACGGTTCCGGTAGAAACCTCCAAAGGACCTAAACTTTCTGTTGTTTCTA
TCGACCATCTTCCATCCTTGTTACCCAGGGAAGCATCAGAGTTTTTTGTC
AGAGACTTATTGCCTTACTTGAAACAGTTACCGGAAAGGAAGACTGCTCC
CGTTTGGGAAAAGAGTAAAGATTTATTTGATCATCATGTCGAAAGACTTT
AATGATATTCTGGTTGTTTAGCTGCTTTGAAGTGTTTCATCTTAAAATAT
ATACTTATTCGTACACAATGCTTACCAAACTCTTATTAGTGTCCAAGTCT
TCTGTAGAGGCAGTTGTTCCGTTCAATAGCACCTCAGCTTCACTGTCAAA
ATCACTGTCCTCTGCCTCAAATTTGGGGGTTGTTTTTTTTACATTCTTCA
AGTCCTCTATGTTTTCATTCATTGTAGTAACTACCGTAAGGCGCTCGCTA
GTAGCATACACTGCAACTTGGTCAAAAGTTTTTAAGCTCCAGACAACAAT
CTTACCATCAGAGGCAACTGATACTAAAAATGAGTCTTTTGAGTCATCGT
CTTGATAAATGCTTATGTCCTTTACGCGAGTTGAATGACCCAAGAGTTTG
TAATCAGGTTGAAGCTTCTCCACATCTCCTAGAAAGCACTCATATGAATA
AAAACAGATCTCCCCATTACTATGACAAGTGATTAAGTATTCTTTTTCTA
GCTGCACAACCTCAATTTTCATTATTGTGGACTGAAAGGGAATATTTGTG
AGAAGCTTTGCGGTCCTAGTATGGTAGACAAATATTCTGTTGACCAAGGC
AACAATAAAATGCTCCCCATCAAAAGACCATTTAACAAAGTGACCGGATT
GTCCTAAAGTATCCTTTCCTTTCATTTTTAGGGTTGATGCCAGCTTGGAA
CTCATGAGGTTCCACAGTCTTATTGTTTTATCGTTACTGACCGAGACTGC
AACTTTTCCACTAGGGTGAAGCCAAGTCATTTACCGCAGCTTTATGACCC
TTCAGCACAGCTACTGGCTCCCAGTCTTTAGTTCTCCAAACGATGATTGA
CCCATCTTCACTTCCTGAAAGTAGCCATTTACCATCCGCATCCCTAGCTT
TAGAACTCTCTCGGCTGAACTTCAAGCAAGTTATCGAACCTGTATGTTGC
AGTAAGCTTCCAATCTCTTTTCTTTTTTGGAGATCATAAATCTTTATATG
CTCGTCGTTAGAGCCGCTAACCAAATACCGCTTTGCCTGATCTAACGCTC
TGATGCTTAAAGAATGAGCTTCGAAGTGAAAAATAGGCTGAAAAATAGGT
GTCTTCTCAGAACTCGGTTCGCAACTGACAGTAACACTAAGACATGATAG
TATGTGCTCATAAGATCCAACTACGATTCGAAACCGAACAGAGGTGCTCT
TATTACTGTTATTTATATTTAACGTCTCCCCCATGTTCGTTATCGCAGTG
TGCAGAATTTTCCTAAACTAATTTTTTTGGTATTCGAGATCGTTGATTAT
TAGCTTACAATCAAACTTCCCTCACCTTTTTCCTTCCATCACACATCTAT
CCACAATTGGCTTGGTTGCATCTGATAGCTAGCTGGCGGAAACATCAGTC
AAAAAACATGAAGACTACTTTCTGAGAGACATAAGTTAAAGCAGTTGCTG
AAAAATCGTCGTTATCCAATTGATAACAGAAGCAACTGAAGAAATAAAAA
ATTGCGCATGCCCGGAGTCGAACCGGG

Pichia pastoris LYS4: (SEQ ID NO: 10) Stop codon 1245-1247

ATCCCCGTATCAATGAAGAGACTTTGTCCGATTTGATTACCAACAAGATG
GATGCTGACCCCGATGCTTACTACGCCAAAACCTTAACAGTAGACCTCTC
CACCATGTCTCCGTACATATCCGGACCAAACTCTGTAAAGATTTCTAATT
CTCTGGAGGATCTGTCCAACAAGAACATGAAGATAAACAAGGCCTATTTG
GTCTCATGTACCAATTCCAGACTGTCCGACATAAGGGCTGCTGCTGATGT
TATCAAGGGTAAGAAAGTTGCTCCTGGTGTCGAGTTTTACATTGCAGCCG
CCTCCAGTGAAGTTCAGAAAGAGGCTGAATCTGATGGTTCGTGGAATTCA
TTGATCGATGCCGGTGCTATTACTTTACCGGCAGGTTGTGGTCCCTGTAT
TGGTCTAGGAACTGGTTTGTTGGAAGAAGGCGAAGTTGGTATTCCGCTA
CCAACAGAAACTTCAAAGGTAGAATGGGGTCAAAGGATGCGCTCGCATTC
TTGGCTTCCCCAGAAGTTGTTGGAGCATCTGCAGTGATGGGTAAGATTGC
TGGACCAGAAGAAGTTGAGGGAAACCCAGTAAAAGGTGTCAGAGACCTTA
AAAAGAGCATAATTATTCACGAACCTGAACAATCGGAATCTGCAGGAGGA
GCTGTGGAAGTTCTTGCTGGTTTCCCCGAGTCGATTGAAGGTGAGCTAAT
TCTCTGTGATGCTGATAACATCAATACTGACGGTATCTATCCAGGAAAAT
ACACTTACCAGGAGGATGTTTCTCGTGAAAAAATGGCCGAAGTCTGTATG
GAGAATTACGACCCAGAATTCGGAAGCAAAACCAAACCGGGCGATATTAT
TGTGTCAGGTTATAACTTTGGAAGAGGGTCTTCAAGAGAGCAAGCGGCTA
CCGCAATCTTAGCCAGAGACATGAAGTTGATTGTGGCAGGTTCCTTTGGT
AATATTTTTTCCAGAAATTCCATTAACAACGCCTTACTGACTCTTGAGAT
CCCTAAGTTAATCAACATGCTAAGAGAAAAGTATTCCAGTAACGAGGAGA
AGGAATTGACCCGAAGAACTGGATGGTTCCTCAAATGGGATGTCAAAGCC
GCTACCGTGACTGTTACTGACGGCAAGAGTGGAGAAGTTGTCTTGAAACA
AAAAGTGGAGAATTGGGAACCAATCTGCAAGATATCATTATTAAAGGCG
GTCTTGAAGGTTGGGTCAAGGCCAAACTGGCGGAAACCAGTACGTAGAGT
GACATTGTCACAATATATTTATTTATTGATAGAATAGAAATTCCTG
TATCTACCTACTAATATACAGAGTGTTTACTAAACCGTCCTTCCCTCTTT

TTCTCTCACTTACAACGAGCCAACTTCCTTGACTACCTCGTCGAAAGAAT
CTTTGTACTCTTCGGCTGTTTTGCTTTCTCCCTTCTTGCTCTTGTTAGCA
TTTGGAACGATCATGACACAAGAAGTTGGGCGCTTGGTAGCTCCAGCAGA
TCCCAGATCCTCCTTAGAAGGTAAGAACAAATATGGAACGTTACTATCCT
CACATAAAACTGGAATATGAGAAATAACATCTGGTGGTGAAATGTCACCT
GCAATGATCACTAACCCTTTCTCTCCCTTTCTTAAGGATTTCACGACCTC
TTTAACACCTCTTCTCACATGCTTGGCTTTGGAAGCCTTCTTGACAGTTT
TGAGAACCTTTTTGTTAAGCTTTTTAGAGGCTAAAGGTTTAGCAAAAGGC
AAAAGTGCAGGCAACTTCTTGTCGTAGTTGTCTTCAGTTTCCTCCTTACT
GGCGCTCTTCTCTTTTTTTGACATTGTTTGATAGTTGAATTATCGGAAAC
TAAAAAAAAATTTCAACTATACCAGCTTACAAAAAAAAATTTAGCACTGA
GAACTTGGTCGTGTCCACTCTATTTTACTAGATATTTGTATCAAGCTTAA
GTAATAATTTGAACTAAGGTCGTGCATTCACAACTTTGCTTTACTATCTC
AGAAAGCAGTACTTCACTTCAGGAAGAGACATAAGGTGAACATGTCTTCA
AAGAAGGACTCTTCCAAGAGAATGTCCCTCTTCGGACCGCTGAAGGGTAC
CGGAATACTTGGATTTGGTCACAATGACACTAAACAGCAGCAT

*Pichia pastoris* ADE2: (SEQ ID NO: 11) Stop codon 1653-1655
AGCTAGGCCGAATGATTGTTGAGGCCGCTAGCAGGCTCAATATCAAGACC
GTGATTCTTGATGATGGTTTTTCACCTGCTAAGCACATTAATGCTGCGCA
AGACCACATCGACGGATCATTCAAAGATGAGGAGGCTATCGCCAAGTTAG
CTGCCAAATGTGATGTTCTCACTGTAGAGATTGAGCATGTCAACACAGAT
GCTCTAAAGAGAGTTCAAGACAGAACTGGAATCAAGATATATCCTTTACC
AGAGACAATCGAACTAATCAAGGATAAGTACTTGCCAAAGGAACATTTGA
TCAAGCACAACATTTCGGTGACAAGTCTCAGGGTATAGAATCTAATGAAA
AGGCGCTGCTTTTGTTTGGAGAAGAGAATGGATTTCCATATCTGTTGAAG
TCCCGGACTATGGCTTATGATGGAAGAGGCAATTTTGTAGTGGAGTCTAA
AGAGGACATCAGTAAGGCATTAGAATTCTTGAAAGATCGTCCATTGTATG
CCGAGAAGTTTGCTCCTTTTGTTAAAGAATTAGCGGTAATGGTTGTGAGA
TCACTGAAGGCGAAGTATTCTCCTACCCAACCGTAGAAACTGTGCACAA
GGACAATATCTGTCATATTGTGTATGCTCCGGCCAGAGTTAATGACACCA
TCCAAAAGAAAGCTCAAATATTAGCTGAAAACACTGTGAAGACTTTCCCA
GGCGCTGGAATCTTCGGAGTTGAGATGTTCCTATTGTCTGATGGAGAACT
TCTTGTAATGAGATTGCTCCAAGGCCGCACAATTCTGGTCACTATACAAT
CGATGCATGTGTAACATCTCAGTTCGAAGCACATGTAAGAGCCATAACTG
GTCTGCCAATGCCACTAGATTTCACCAAACTATCTACTTCCAACACCAAC
GCTATTATGCTCAATGTTTTGGGTGCTGAAAAATCTCACGGGGAATTAGA
GTTTTGTAGAAGAGCCTTAGAAACACCCGGTGCTTCTGTATATCTGTACG
GAAAGACCACCCGATTGGCTCGTAAGATGGGTCATATCAACATAATAGGA
TCTTCCATGTTGGAAGCAGAACAAAAGTTAGAGTACATTCTAGAGAATCA
ACCCACTTACCATCCAGTACTGTATCAGCTGACACTAAACCGTTGGTTGG
AGTTATCATGGGTTCAGACTCTGATCTACCTGTGATTTCGAAAGGTTGCG ATATTTTAAAACAGTTTGGTGTTCCATTCGAAGTTACTATTGTCTCTGCT
CATAGAACACCACAGAGAATGACCAGATATGCCTTTGAAGCCGCTAGTAG
AGGTATCAAGGCTATCATTGCAGGTGCTGGTGGTGCTGCTCATCTTGCAG
GAATGGTTGCTGCCATGACTCCGTTGCCAGTCATTGGTGTTCCTGTCAAG
GGCTCTACGTTGGATGGTGTAGACTCGCTACACTCGATTGTCCAAATGCC
TAGAGGTGTTCCTGTGGCTACGGTTGCTATCAACAACGCCACCAATGCCG
CTCTGTTGGCCATCAGGATTTTAGGTACAATTGACCACAAATGGCAAAAG
GAAATGTCCAAGTATATGAATGCAATGGAGACCGAAGTGTTGGGGAAGGC
ATCCAACTTGGAATCTGAAGGGTATGAATCCTATTTGAAGAATCGTCTTT
GAATTTAGTATTGTTTTTTAATAGATGTATATATAATAGTACACGTAACT
TATCTATTCCATTCATAATTTTATTTTAAAGGTTCGGTAGAAATTTGTCC
TCCAAAAGTTGGTTAGAGCCTGGCAGTTTTGATAGGCATTATTATAGAT
TGGGTAATATTTACCCTGCACCTGGAGGAACTTTGGAAAGAGCCTCATGT
GCTCTAAAAGGATGTCAGAATTCCAACATTTCAAAATTATATCTGCATGC
GTCTGTAATACTGGAACTGTTATTTTTCTGGTCAGGATTTCACCGCTCTT
GTCGTCATGTTTCTCGTCGTCTGAAAGTAAACTGACTTTCCTCTTTCCAT
AAACACAAAAATCGATTGCAACTTGGTTATTCTTGAGATTGAAATTTGCT
GTGTCTTCAGTGCTTAGCTGAATATCAACAAAGTTACTTAGTACTAATAA
CGAAGCACTATGGTAAGTGGCATAACATAGTGGTATTGAAGCGAACAGTG
GATATTGAACCCAAGCATTGGCAACATCTGGCTCTGTTGATACTGATCCG
GATCGTTTGGCACCAATTCCTGAAACGGCGTAGTGCCACCAAGGTTTCGA
TTTGAGAACAGGTTCATCATCAGAGTCAACCACCCCAATGTCAATGGCAG
GCTCCAACGAAGTAGGTCCAACAACAACAGGAAGTATTTGACCTTGAAGA
TCTGTTCCTTTATGATCCACCACACCTTGCCCCAATTCCAATAACTTTAC
CAGTCCCGATGCAGACATGATAACTGGTACTAATGATCTCCATTGATTTT
CGTCGGCACTACGTAAAGCCTCCAAAAATGAATTCAGAATATCTTCTGAA
ACTAGATTCTGCTTCTGTGATTCAAGCATTGCTTTATGTAGACATCTCTT
GAATAAAAGCAATTCTCCACATATTGGTGTGTGTAAGATAGATCTGGAAA
GATGTATCTGGAATAGTCCAGTCAACGTTGTGCAATTGATTAGCATTACC
TTACTGTGAACATCTCTATCTACAACAACAGACTCAATTCGATAGACGTT
CCGGGAAAGTTTTTCAAGCGCATTCAGTTTGCTGTTGAACAAAGTGACTT
TGCTTTCCAATGTGCAAATACCCCTGTATATCAAGTCCATCACATCACTC
AAGACCTTGGTGGAAAAGAATGAAACAGCTGGAGCATAATTTTCGAATGA
ATTAGGTAAGGTCACTTCATCCTTATCTGTTGTAATGCTATAATCAATAG
CGGAACTAACATCTTCCCATGTAACAGGTTTCTTGATCTCTGAATCTGAA
TCTTTATTTGAAAAAGAATTGAAAAAAGACTCATCACTCATTGGGAATTC
AAGGTCATTAGGGTATTCCATTGTTAGTTCTGGTCTAGGTTTAAAGGGAT
CACCTTCGTTAAGACGATGGAAAATAGCTAATCTGTACAATAACCAGATA
CTTCTAACGAAGCTCTCTCTATCCATCAGTTGACGTGTTGAGGATATCTG
AACTAGCTCTTTCCACTGCGAATCAGGCATGCTCGTATAGCTGGCAAGCA -continued

TGTTATTCAGCTTTACCAAGTTAGAAGCCCTTTGGAAACCATCTATAGAT

TCCCGAAAAAACTTATACCCACTGAGGGTTTCACTGAGCATAGTCAGTGA

CATCAAAGAGCATTTCAAATCCATCTCAGGCCAGTAT

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A vector for inserting heterologous genes of interest into a target DNA sequence in the genome of a host cell adjacent to an open reading frame (ORF) comprising 5' to 3' with reference to the vector:
   (a) a first homologous vector DNA sequence capable of homologous recombination with a 5' flanking region of the target DNA sequence, which first vector DNA sequence includes an open reading frame (ORF) of the target DNA sequence and ends at its 3' end with a stop codon of the open reading frame (ORF) in the target DNA sequence;
   (b) a heterologous transcription termination DNA sequence operably linked to the 3' end of the first vector DNA sequence such that the transcription termination sequence is adjacent to the stop codon for the ORF of part (a);
   (c) a DNA sequence comprising one or more expression cassettes linked to the 3' end of the heterologous transcription termination DNA sequence of part (b); and
   (d) a second homologous vector DNA sequence capable of homologous recombination with a 3' flanking region of the target DNA sequence, said second homologous vector DNA sequence linked to the 3' end of the DNA sequence comprising the one or more expression cassettes of part (c);

wherein the vector is capable of undergoing homologous recombination with the target DNA sequence to provide an integrated vector construct, and wherein the integrated vector construct creates an intergenic region in the host genome which does not duplicate or delete host genomic sequences and does not disrupt functional expression of the target gene.

2. The vector of claim 1, wherein the vector has at least two expression cassettes and one of the expression cassettes encodes a detectable or selectable marker.

3. The vector of claim 1, wherein at least one expression cassette encodes a fusion protein comprising a signal sequence.

4. The vector of claim 1, wherein the ORF is selected from the group of genes consisting of HIS4, ARG4, ADE1, ADE2, HIS3, PRO1, PRO2, TRP1, TRP2, TRP5, LYS1, LYS4, and THR1.

5. The vector of claim 2, wherein the selectable marker is counter-selectable.

6. A vector for inserting heterologous genes of interest into a target DNA sequence in the genome of a host cell adjacent to an open reading frame (ORF) comprising 5' to 3' with reference to the vector:
    (a) a first homologous vector DNA sequence capable of homologous recombination with a 5' flanking region of the target DNA sequence;
    (b) a DNA sequence comprising one or more expression cassettes linked to the 3' end of the first homologous vector DNA sequence of part (a);
    (c) a heterologous promoter DNA sequence linked to the 3' end of the DNA sequence comprising one or more expression cassettes of part (b); and
    (d) a second homologous vector DNA sequence capable of homologous recombination with a 3' flanking region of the target DNA sequence, which second vector DNA sequence at its 5' end comprises the open reading frame (ORF) of the target DNA sequence and begins with the start codon of the ORF and contiguous with the 3' end of the heterologous promoter DNA sequence of part (c);
    wherein the vector is capable of undergoing homologous recombination with the target DNA sequence, to provide an integrated vector construct wherein the integrated vector construct creates an intergenic region in the host genome which does not duplicate or delete host genomic sequences and does not disrupt functional expression of the target gene.

7. The vector of claim 6, wherein the vector has at least two expression cassettes and one of the expression cassettes encodes a detectable or selectable marker.

8. The vector of claim 6, wherein at least one expression cassette encodes a fusion protein comprising a signal sequence.

9. The vector of claim 6, wherein the ORF is selected from the group of genes consisting of HIS4, ARG4, ADE1, ADE2, HIS3, PRO1, PRO2, TRP1, TRP2, TRP5, LYS1, LYS4, and THR1.

10. The vector of claim 7, wherein the selectable marker is counter-selectable.

11. A vector for inserting heterologous genes of interest into a target DNA sequence in the genome of a host cell wherein the vector has the following arrangement, from the 5' to the 3' direction:
    a) a 5' flanking sequence homologous to the 5' side of an insertion site in a target sequence in the host genome, which includes an open reading frame (ORF);
    b) a first transcription termination sequence;
    c) one or more expression cassettes wherein each expression cassette comprises (i) a promoter sequence; (ii) a sequence of interest; and (iii) a second transcription termination sequence; and
    d) a 3' flanking sequence homologous to the 3' side of the insertion site of the target sequence.

12. A vector for inserting heterologous genes of interest into a target DNA sequence in the genome of a host cell wherein the vector has the following arrangement, from the 5' to the 3' direction:
    a) a 5' flanking sequence homologous to the 5' side of an insertion site in a target sequence in the host genome, which includes sequence up to an open reading frame (ORF);
    b) one or more expression cassettes wherein each expression cassette comprises (i) a promoter sequence; (ii) a sequence of interest; and (iii) a second transcription termination sequence;
    c) a promoter sequence for regulating expression of the ORF; and
    d) a 3' flanking sequence homologous to the 3' side of the insertion site in the target sequence in the host genome, which includes the ORF and its start codon.

\* \* \* \* \*